(12) United States Patent
Cho

(10) Patent No.: US 7,273,849 B2
(45) Date of Patent: Sep. 25, 2007

(54) PROAPOLIPOPROTEINA-I MUTANT AND PHARMACEUTICAL COMPOSITION COMPRISING THE SAME FOR PREVENTION AND TREATMENT OF ATHEROSCLEROSIS AND HYPERLIPIDEMIA

(76) Inventor: Kyung-Hyun Cho, 104-605 Siji-Taewang 6-cha APT, Sawol-dong, Suseong-gu, Daegu (KR)

( * ) Notice: Subject to any disclaimer, the term of this patent is extended or adjusted under 35 U.S.C. 154(b) by 0 days.

(21) Appl. No.: 11/116,319

(22) Filed: Apr. 28, 2005

(65) Prior Publication Data
US 2005/0287636 A1 Dec. 29, 2005

(30) Foreign Application Priority Data
Jun. 25, 2004 (KR) .............. 10-2004-0048354

(51) Int. Cl.
*A61K 38/00* (2006.01)
*C07K 1/00* (2006.01)
(52) U.S. Cl. .................... 514/12; 530/350
(58) Field of Classification Search ............ 530/350; 514/12
See application file for complete search history.

(56) References Cited

U.S. PATENT DOCUMENTS 5,059,528 A * 10/1991 Bollen et al. ............ 435/69.4
5,643,757 A 7/1997 Malik et al.
5,876,968 A 3/1999 Sirtori et al.
5,990,081 A 11/1999 Ageland et al.
6,897,039 B2 * 5/2005 Graversen et al. ......... 435/69.1

FOREIGN PATENT DOCUMENTS

| WO | WO90/12879 | 11/1990 |
|----|-----------|---------|
| WO | WO94/13819 | 6/1994 |
| WO | WO96/37608 | 11/1996 |

OTHER PUBLICATIONS

Jerzy-Roch Nofer et al., "HDL and Arteriosclerosis: beyond reverse cholesterol transport," Atherosclerosis 161 (2002), pp. 1-16.
Jere P. Segrest et al., "Structure and function of apolipoprotein A-1 and high-density lipoprotein," Current Opinion in Lipidology, (2000), pp. 105-115.
Olga Stein, et al., "Atheroprotective mechanism of HDL," Atherosclerosis 144 (1999), pp. 285-301.
David K. Spady, "Reverse Cholesterol Transport and Atherosclerosis Regression," Circulation 100, (Aug. 10, 1999), pp. 576-578.
George H. Rothblat et al., "Cell cholesterol efflux: integration of old and new observations provides new insights," Journal of Lipid Research, vol. 40, (1999), pp. 781-796.

(Continued)

*Primary Examiner*—Maryam Monshipouri
(74) *Attorney, Agent, or Firm*—Finnegan, Henderson, Farabow, Garrett & Dunner, L.L.P.

(57) ABSTRACT

The proapoA-I mutants of the present invention exhibit superior LDL-antioxidant activities over the wild-type proapoA-I and higher efficiencies for delivering cholesterol to hepatocytes than the previously reported apoA-I-R173C, and thus they can be effectively used for prevention and treatment of hyperlipidemia or atherosclerosis.

6 Claims, 13 Drawing Sheets

Met-His-His-His-His-His-His-Ser-Ser-Gly-Leu-Val-Pro-Arg-Gly-Ser-
Gly-Met-Lys-Glu-Thr-Ala-Ala-Ala-Lys-Phe-Glu-Arg-Gln-His-Met-Asp-
Ser-Pro-Asp-Leu-Gly-Thr-Asp-Asp-Asp-Asp-Lys-Ala-Met-Ala-His-Phe-
Trp-Gln-Gln-Ala-Pro-Arg-Pro-Pro-Thr-Pro-Asp-Glu-Pro-Pro-Gln-Ser-
Pro-Trp-Asp-Arg-Val-Lys-Asp-Leu-Ala-Thr-Val-Tyr-Val-Asp-Val-Leu-
Lys-Asp-Ser-Gly-Arg-Asp-Tyr-Val-Ser-Gln-Phe-Glu-Gly-Ser-Ala-Leu-
Gly-Lys-Gln-Leu-Asn-Leu-Lys-Leu-Leu-Asp-Asn-Trp-Asp-Ser-Val-Thr-
Ser-Thr-Phe-Ser-Lys-Leu-Arg-Glu-Gln-Leu-Gly-Pro-Val-Thr-Gln-Glu-
Phe-Trp-Asp-Asn-Leu-Glu-Lys-Glu-Thr-Glu-Gly-Leu-Arg-Gln-Glu-Met-
Ser-Lys-Asp-Leu-Glu-Glu-Val-Lys-Ala-Lys-Val-Gln-Pro-Tyr-Leu-Asp-
Asp-Phe-Gln-Lys-Lys-Trp-Gln-Glu-Glu-Met-Glu-Leu-Tyr-Arg-Gln-Lys-
Val-Glu-Pro-Leu-Arg-Ala-Glu-Leu-Gln-Glu-Gly-Ala-Arg-Gln-Lys-Leu-
His-Glu-Leu-Gln-Glu-Lys-Leu-Ser-Pro-Leu-Gly-Glu-Glu-Met-Arg-Asp-
Arg-Ala-Arg-Ala-His-Val-Asp-Ala-Leu-Arg-Thr-His-Leu-Ala-Pro-Tyr-
Ser-Asp-Glu-Leu-Arg-Gln-Arg-Leu-Ala-Ala-Arg-Leu-Glu-Ala-Leu-Lys-
Glu-Asn-Gly-Gly-Ala-Arg-Leu-Ala-Glu-Tyr-His-Ala-Lys-Ala-Thr-Glu-
His-Leu-Ser-Thr-Leu-Ser-Glu-Lys-Ala-Lys-Pro-Ala-Leu-Glu-Asp-Leu-
Arg-Gln-Gly-Leu-Leu-Pro-Val-Leu-Glu-Ser-Phe-Lys-Val-Ser-Phe-Leu-
Ser-Ala-Leu-Glu-Glu-Tyr-Thr-Lys-Lys-Leu-Asn-Thr-Gln

OTHER PUBLICATIONS

J. Koizumi, et al., "Behavior of human apolipoprotein A-I: phospholipid and apolHDL:phospholipid complexes in vitro and after injection into rabbits," Journal of Lipid Research, vol. 29, (1988), pp. 1405-1415.

David J. Gordon and Basil M. Rifkind, "High-density lipoprotein—the clinical implications of recent studies," The New England Journal of Medicine 321, (Nov. 9, 1989), pp. 1311-1316.

Giulia Chiesa and Cesare R. Sirtori, "Recombinant apolipoprotein A-$1_{Milano}$: a novel agent for the induction of regression of atherosclerotic plaques," Annuals of Medicine 35, (2003), pp. 267-273.

Marian C. Cheung et al., "Altered particle size distribution of apolipoprotein A-I-containing lipoproteins in subjects with coronary artery disease," Journal of Lipid Research, vol. 32, (1991), pp. 383-394.

J.C. Fruchart and G. Ailhaud, Apolipoprotein A-Containing Lipoprotein Particles: Physiological Role, Quantification, and Clinical Significance,: Clinical Chemistry, vol. 38, No. 6, (1992), pp. 793-797.

Edward M. Rubin, et al., "Inhibition of early atherogenesis in transgenic mice by human apolipoprotein AI," Nature, vol. 353, (Sep. 19, 1991), pp. 265-267.

Chris Paszty et al., "Apolipoprotein AI Transgene Corrects Apolipoproten E Defeciency-induced Atherosclerosis in Mice," J. Clin. Invest., vol. 94, (Aug. 1994), pp. 899-903.

Alexander C. Liu, et al., "Human apolipoprotein A-I prevents atherosclerosis associated with apolipoprotein[a] in transgenic mice," Journal of Lipid Research, Vo. 35, (1994), pp. 2263-2267.

Prediman K. Shah, et al., "Effects of Recombinant Apolipoprotein A-$1_{Milano}$ on Aortic Atherosclerosis in Apolipoprotein E-Deficient Mice," Circulation 97 (1998) pp. 780-785.

Prediman K. Shah et al., "High Dose Recombinant Apolipoprotein A-$1_{Milano}$ Mobilizes Tissue Cholesterol and Rapidly Reduces Plaque Lipid and Macrophage Content in Apolipoprotein E-Deficient Mice," Circulation 103, (2001), pp. 3047-3050.

Andrew G. Lacko and Norman E. Miller, "International Symposium on the Role of HDL in Disease Prevention: Report on a Meeting," Journal of Lipid Research, vol. 38 (1997), pp. 1267-1273.

Steven E. Nissen et al., "Effect of Recombinant ApoA-1 Milano on Coronary Atherosclerosis in Patients with Acute Coronary Syndromes," JAMA 290, No. 17, (Nov 5, 2003), pp. 2292-2300.

Steven E. Nissen et al., "Effect of Intensive Compared with Moderate Lipid-Lowering Therapy on Progression of Coronary Atherosclerosis," JAMA 291, No. 9, (Mar. 3, 2004), pp. 1071-1080.

Kyung-Hyun Cho and Ana Jonas, "A Key Point Mutation (V156E)Affects the Structure and Functions of Human Apolipoprotein A-I," The Journal of Biological Chemistry, vol. 275, No. 35, (Sep. 1, 2000), pp. 26821-26827.

Charles E. Matz and Ana Jonas, Micellar Complexes of Human Apolipoprotein A-1 with Phosphatidylcholines and Cholesterol Prepared from Cholate-Lipid Dispersions, The Journal of Biological Chemistry, vol. 257, No. 8, (Apr. 25, 1982), pp. 4535-4538.

James V. Staros, "N-Hydroxysulfosuccinimide Active Esters: Bis (N-hydroxysulfosuccinimide) Esters of Two Dicarboxylic Acids Are Hydrophilic, Membrane-Impermeant, Protein Cross-Linkers," Biochemistry, vol. 21, No. 17, (1982), pp. 3950-3955.

Zhen Jia et al., "Thiol-bearing synthetic peptides retain the antioxidant activity of apolipoprotein A-$I_{Milano}$." Biochemical and Biophysical Research Communications 297, (2002), pp. 206-213.

* cited by examiner

Fig. 1

Met-His-His-His-His-His-His-Ser-Ser-Gly-Leu-Val-Pro-Arg-Gly-Ser-
Gly-Met-Lys-Glu-Thr-Ala-Ala-Ala-Lys-Phe-Glu-Arg-Gln-His-Met-Asp-
Ser-Pro-Asp-Leu-Gly-Thr-Asp-Asp-Asp-Asp-Lys-Ala-Met-Ala-His-Phe-
Trp-Gln-Gln-Ala-Pro-Arg-Pro-Pro-Thr-Pro-Asp-Glu-Pro-Pro-Gln-Ser-
Pro-Trp-Asp-Arg-Val-Lys-Asp-Leu-Ala-Thr-Val-Tyr-Val-Asp-Val-Leu-
Lys-Asp-Ser-Gly-Arg-Asp-Tyr-Val-Ser-Gln-Phe-Glu-Gly-Ser-Ala-Leu-
Gly-Lys-Gln-Leu-Asn-Leu-Lys-Leu-Leu-Asp-Asn-Trp-Asp-Ser-Val-Thr-
Ser-Thr-Phe-Ser-Lys-Leu-Arg-Glu-Gln-Leu-Gly-Pro-Val-Thr-Gln-Glu-
Phe-Trp-Asp-Asn-Leu-Glu-Lys-Glu-Thr-Glu-Gly-Leu-Arg-Gln-Glu-Met-
Ser-Lys-Asp-Leu-Glu-Glu-Val-Lys-Ala-Lys-Val-Gln-Pro-Tyr-Leu-Asp-
Asp-Phe-Gln-Lys-Lys-Trp-Gln-Glu-Glu-Met-Glu-Leu-Tyr-Arg-Gln-Lys-
Val-Glu-Pro-Leu-Arg-Ala-Glu-Leu-Gln-Glu-Gly-Ala-Arg-Gln-Lys-Leu-
His-Glu-Leu-Gln-Glu-Lys-Leu-Ser-Pro-Leu-Gly-Glu-Glu-Met-Arg-Asp-
Arg-Ala-Arg-Ala-His-Val-Asp-Ala-Leu-Arg-Thr-His-Leu-Ala-Pro-Tyr-
Ser-Asp-Glu-Leu-Arg-Gln-Arg-Leu-Ala-Ala-Arg-Leu-Glu-Ala-Leu-Lys-
Glu-Asn-Gly-Gly-Ala-Arg-Leu-Ala-Glu-Tyr-His-Ala-Lys-Ala-Thr-Glu-
His-Leu-Ser-Thr-Leu-Ser-Glu-Lys-Ala-Lys-Pro-Ala-Leu-Glu-Asp-Leu-
Arg-Gln-Gly-Leu-Leu-Pro-Val-Leu-Glu-Ser-Phe-Lys-Val-Ser-Phe-Leu-
Ser-Ala-Leu-Glu-Glu-Tyr-Thr-Lys-Lys-Leu-Asn-Thr-Gln

Fig. 2 c gacgacgac gacaag▼gcca tggcccattt ctggcagcaa gctccacgtc caccgacacc
　　　　　　　　Protein cleavage site by enterokinase
c gatgaaccc ccccagagcc cctgggatcg agtgaaggac ctggccactg tgtacgtgga
　1st amino acid of apoA-1
tgtgctcaaa gacagcggca gagactatgt gtcccagttt gaaggctccg ccttgggaaa acagctaaac ctaaaacttc tagacaactg ggacagcgtg acctccacct tcagcaagct gcgcgaacag ctcggccctg tgacccagga attctgggat aacctggaaa aggagacaga gggcctgagg caggagatga gcaaggatct ggaggaggtg aaggccaagg tgcagcccta cctggacgac ttccagaaga agtggcagga ggagatggag ctctaccgcc agaaggtgga gccgctgcgc gcagagctgc aggagggcgc gcgccagaag ctgcacgagc tgcaagagaa gctgagccca ctgggcgagg agatgcgcga ccgcgcgcgc gcccatgtgg acgcgctccg gacgcatctg gcccccacta gcgacgagct gcgccagcgc ttggccgcgc gccttgaggc tctcaaggag aacggcggcg ccaggctagc cgagtaccac gccaaggcca ccgagcatct gagcacgctc agcgagaagg ccaagcccgc gctcgaggac ctccgccaag gcctgctgcc cgtgctggag agcttcaagg tcagcttcct gagcgctctc gaggagtaca ctaagaagct caacacccag taata
　　　　　　Termination codon

A

B

PROAPOLIPOPROTEINA-I MUTANT AND PHARMACEUTICAL COMPOSITION COMPRISING THE SAME FOR PREVENTION AND TREATMENT OF ATHEROSCLEROSIS AND HYPERLIPIDEMIA

FIELD OF THE INVENTION

The present invention relates to a proapolipoproteinA-I (proapoA-I hereinafter) mutant and a pharmaceutical composition comprising the same for prevention and treatment of hyperlipidemia and atherosclerosis. In particular, the present invention relates to the proapoA-I mutant, a proapolipoprotein mutant, comprising Ala-His-Phe-Trp-Gln-Gln at the amino terminal of apolipoprotein(apoA-I) wherein a mutation is introduced in the proapolipoprotein(proapoA-I) at any one of the $154^{th}$, $155^{th}$, $156^{th}$, $157^{th}$ and $158^{th}$ amino acids of the apoA-I; a nucleic acid encoding the mutant, a recombinant vector containing the nucleic acid; a cell transformed by the vector; and a pharmaceutical composition comprising the mutant for prevention and treatment of hyperlipidemia or atherosclerosis.

BACKGROUND OF THE INVENTION

High-density lipoprotein(HDL) plays an important role in delivering triglyceride and cholesterol by means of coupling to lipid in blood, promoting excretion of excess cholesterol left after being used by peripheral cells, activating enzymes, and inhibiting formation of atherosclerotic plaque by inhibiting oxidation of low-density lipoprotein(LDL), which confers high resistance against cardiocirculatory diseases(Nofer et al., 2002, Atherosclerosis 161:1-16).

These positive functions of HDL are regulated by apolipoproteinA-I(apoA-I), a major protein accounting for about 70% of apolipoproteins that constitute HDL. It has been well known from several clinical reports that if in-blood concentration of apoA-I is too low or there is a problem in the function or structure of apoA-I, HDL does not exhibit these positive functions, and it is often connected to an outbreak of cardiovascular diseases(Segrest et al., 2000, Curr. Opin. Lipidol. 11:105-115).

Atherosclerosis, a cardiovascular disease, is one of the most frequent causes of deaths in industrialized countries. An immediate cause of the disease is as follows: cholesterols are generally deposited on the walls of blood vessels, and the deposited cholesterols are clotted with cells' necrotizing matters to form plaques, which results in atherosclerosis thereby increasing the risk of myocardial infarction or a stroke.

It has been found for the past several decades that there is an inverse proportional relationship between HDL and prevalence of atherosclerosis or hyperlipidemia. Further, it has been understood that apoA-I as a major component of HDL plays an important role in anti-atherosclerosis or anti-hyperlipidernia effect of HDL by stimulating a reverse cholesterol transport(RCT) pathway from the peripheral tissue to the liver(Stein et al., 1999, Atherosclerosis 144: 285-301; Spady, 1999, Circulation 100:576-578; Franceschini et al., 1991, Atherosclerosis 88:99-107; Rothblat et al., 1999, J. Lipid Res. 40:781-796).

ApoA-I is a single polypeptide chain consisting of 243 amino acids with a molecular weight of 28 kDa which contains 8 repeat unit domains consisting of 11 or 22 amino acids. The ratio of alpha helical secondary structure forming HDL in apoA-I is up to 60-75%, and apoA-I is easy to denature and renature its tertiary structure.

Several studies have disclosed that apoA-I, a mutant thereof and HDL are effective in preventing atherosclerosis and treating plaque degeneration(Koizumi et al., 1988, J. Lipid Res. 29:1405-1415; Gordon & Rifkind, 1989, N. Engl. J. Med. 321:1311-1316; Gordon et al., 1989, Circulation 79:8-15; Chiesa & Sirtori, 2003, Ann. Med. 35:267-273). Further, the importance of HDL has been continuously mentioned(Miller, 1987, Am. Heart J. 113:589-597; Cheung et al., 1991, J. Lipid Res. 32:383-394; Fruchart & Ailhaud, 1992, Clin. Chem. 38:793-797).

A direct explanation for the role of apoA-I can be obtained from an experiment using a tansgenic animal. For example, the expression of apoA-I transfected into an artheroma sclerosis mouse model caused by a high fat diet lowered the progress of aortic diseases(Rubin et al., 1991, Nature 353: 265-267). Further, apoA-I transgene suppressed artheroma sclerosis in apoE deficient mouse and apo(a) genetic mutant mouse models(Paszty et al., 1994, J. Clin. Invest. 94:899-903; Plump et al., 1994, Proc. Natl. Acad. Sci. USA 91:9607-9611; Liu et al., 1994, J. Lipid Res. 35:2263-2267; Shah et al., 1998, Circulation 97:780-785; Shah et al., 2001, Circulation 103:3047-3050). In particular, Shah et al has proved that in an apo E-deficient mouse model, apoA-I Milano significantly decreases arterial lesions and reduces the ratio of lipids and macrophages in the lesion by 40% or more (Shah et al., 1998, Circulation 97:780-785; Shah et al., 2001, Circulation 103:3047-3050).

The studies for applying apoA-I and a recombinant apoA-I to a clinical trial have been started by UCB Belgium (Pharmaprojects, Oct. 27, 1995; IMS R&D Focus, Jun. 30, 1997; Drug Status Update, 1997, Atherosclerosis 2:261-265; M. Eriksson at Congress, "The Role of HDL in Disease Prevention", Nov. 7-9, 1996, Fort Worth; Lacko & Miller, 1997, J. Lipid. Res. 38:1267-1273; PCT Publication No: WO94/13819) and Bio-Tech(Pharmaprojects, Apr. 7, 1989).

Recently, it has been reported that as a result of intravenous injection of ETC-216(apoA-I Milano HDL agent) developed by Esperion Therapeutics Inc. merged with Pfizer Inc. into 123 patients having cardiovascular diseases, arteriosclerotic plaques in progress are markedly reduced in a short period of time, which demonstrates the HDL' therapeutic effect(Nissen et al., 2003, JAMA 290:2292-2300). Further, the similar results(Nissen et al., 2004, JAMA 291: 1071-1080) to the above have enhanced more the pharmacological effect and potential market value of HDL.

As described above, the studies on apoA-I and mutants thereof have been actively progressed by several foreign pharmaceutical companies(Table 1).

TABLE 1

Patents related to apoA-I mutants

| Patent | Mutant | Disclosure |
| --- | --- | --- |
| U.S. Pat. No. 5,876,968 (Pharmacia & Upjohn AB) | apoA-I mutant (R173C, MILANO) designated apolipoproteinA-I-Milano | The agent comprising the mutant can be used for preventing thrombosis and as a prodrug of a monomer. It has been suspected that blood half-life is prolonged due to the presence of apo-A-I-Milano, but there is no substantial evidence. |
| U.S. Pat. No. 5,643,757 (American cyanamid Co) | | A method for preparing human apolipoproteinA-I using an E. coli expression system is disclosed. |
| U.S. Pat. No. | | A method for treating atherosclerosis |

TABLE 1-continued

Patents related to apoA-I mutants

| Patent | Mutant | Disclosure |
|---|---|---|
| 5,990,081 (Pharmacia & Upjohn AB) | | or cardiovascular diseases by administering a therapeutic amount of apolipoprotein A or E is disclosed. |
| WO 96/37608 (RHONE POULENC RORER SA et al) | A mutant of apolipoproteinA-I having a cycteine residue at the 151$^{st}$ position (R151C, PARIS) | Monomers can form a dimer via a di-sulfide bond between them due to the presence of cysteine reside in their amino acid sequences. |
| WO 90/12879 (Sirtori Cesareet al) | (R173C, MILANO) | Preparation of apo-I and apoA-IM in yeast and the use as a therapeutic agent for artherisclerosis and cardio-vascular diseases thereof. |
| WO 94/13819 (Pharmacia & Upjohn AB) | (R173C, MILANO) | Preparation of apo-I and apoA-IM in E. coli and the use as a therapeutic agent for artherisclerosis and cardiovascular diseases thereof. |

Since apoA-I mutants as disclosed in the above patents are discovered in nature, when the mutants are expressed in a certain expression host cell, apoA-I has an unstable structure or shows a protein fracture phenomenon in the host cell during the expression, which results in causing the problem of reducing yields.

Meanwhile, the studies on proapolipoproteinA-I (proapoA-I) have been started recently, and reported that proapoA-I shows a good structural stability during the expression without causing any functional difference as compared with apoA-I.

Accordingly, in order to develop a proapoA-I mutant and not an apoA-I mutant naturally obtained, the present inventors have endeavored to analyze the sixth helix domain corresponding to the 143$^{rd}$-164$^{th}$ amino acid positions of proapoA-I and prepare proapoA-I mutants by substituting a specific amino acid in the sixth helix domain with another amino acid. It has been confirmed that the proapoA-I mutants of the present invention have higher therapeutic effects than the previously reported mutants.

SUMMARY OF THE INVENTION

Accordingly, an object of the present invention is to provide a proapoA-I mutant, a proapolipoprotein mutant comprising Ala-His-Phe-Trp-Gln-Gln at the amino terminal of apolipoprotein(apoA-I) wherein a mutation is introduced in the proapolipoprotein(proapoA-I) at any one of the 154$^{th}$, 155$^{th}$, 156$^{th}$, 157$^{th}$ and 158$^{th}$ amino acids of the apoA-I.

Another object of the present invention is to provide a nucleic acid encoding the mutant; a recombinant vector containing the nucleic acid; and a cell transformed by using the vector.

Another object of the present invention is to provide a pharmaceutical composition comprising mutants for prevention and treatment of atherosclerosis or hyperlipidemia.

BRIEF DESCRIPTION OF THE DRAWINGS

The above and other objects and features of the present invention will become apparent from the following description of the invention, when taken in conjunction with the accompanying drawings, wherein:

FIG. 1 shows the amino acid sequences of proapoA-I and apoA-I, wherein the underlined part is the amino acid sequence of apoA-I;

FIG. 2 shows the nucleotide sequence of proapoA-I;

Figure 4:
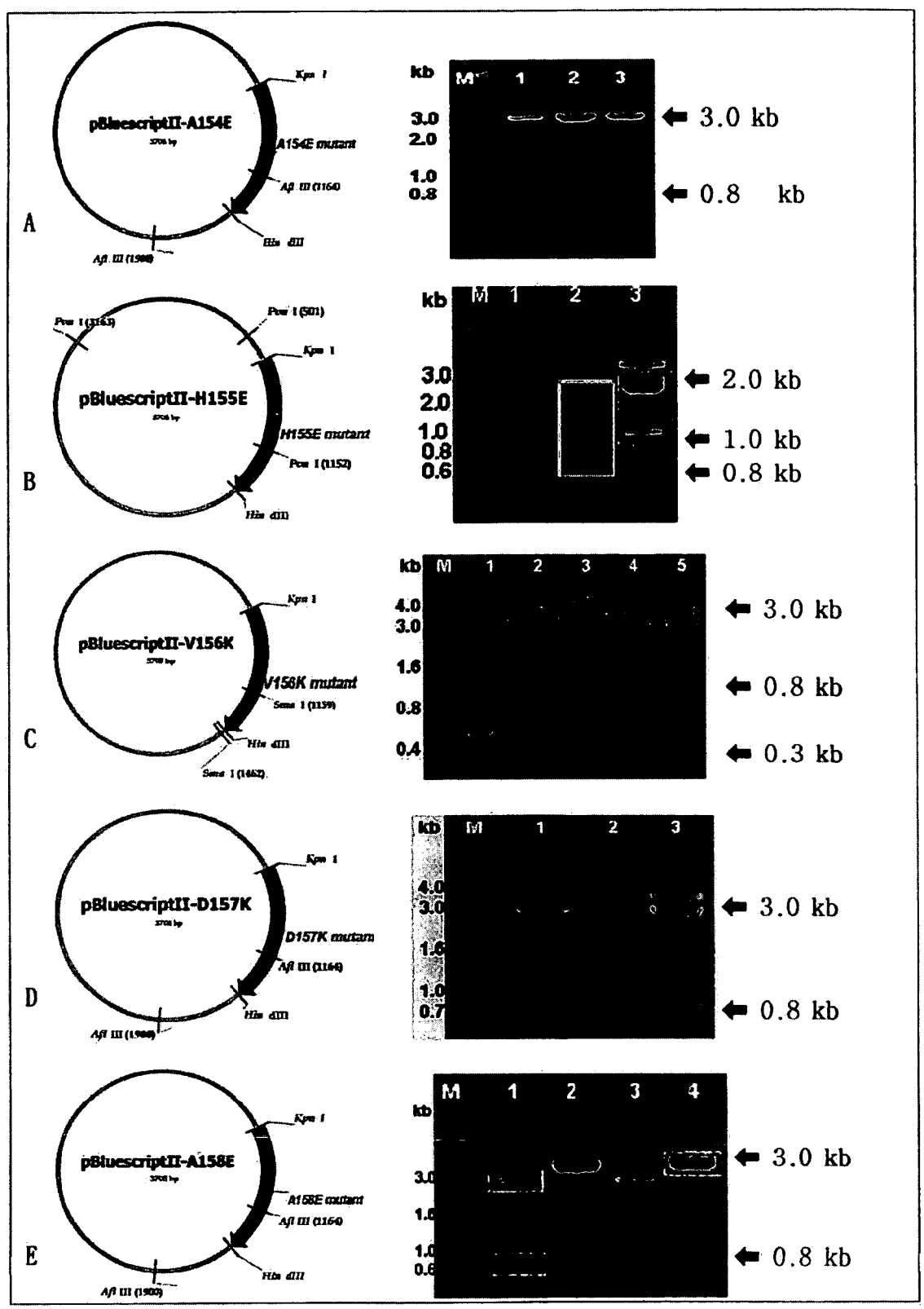

M: 1 kb plus DNA ladder marker,

Lanes 1 and 2: pBlueScriptII-proapoA-I digested with KpnI/HindIII;

FIG. 4 shows the results of confirming the selection of proapoA-I mutants by restriction enzyme treatment

| A: A154E, | B: H155E, |
|---|---|
| C: V156K, | D: D157K, |
| E: A158E; | |

FIG. 5A-B shows the results of cloning proapoA-I mutants into expression vector pET30a, respectively(vector size: 5.6 kb, insert size: 0.8 kb)

| 1: A154E, | 2: H155E, |
|---|---|
| 3: V156K, | 4: A158E; |

Figure 6:
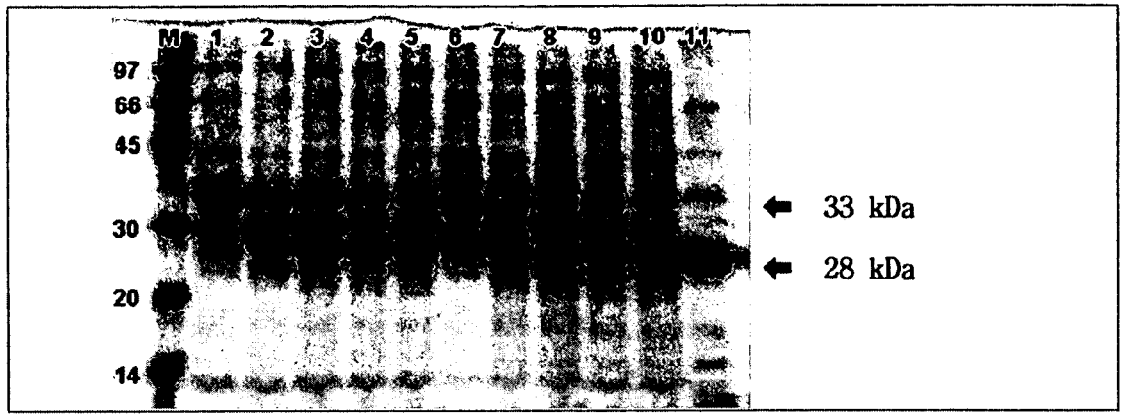
Figure 7:
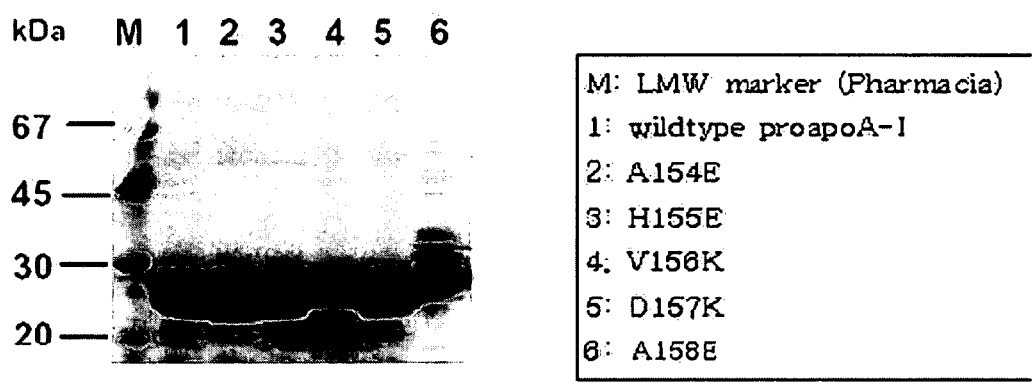
Figure 8:
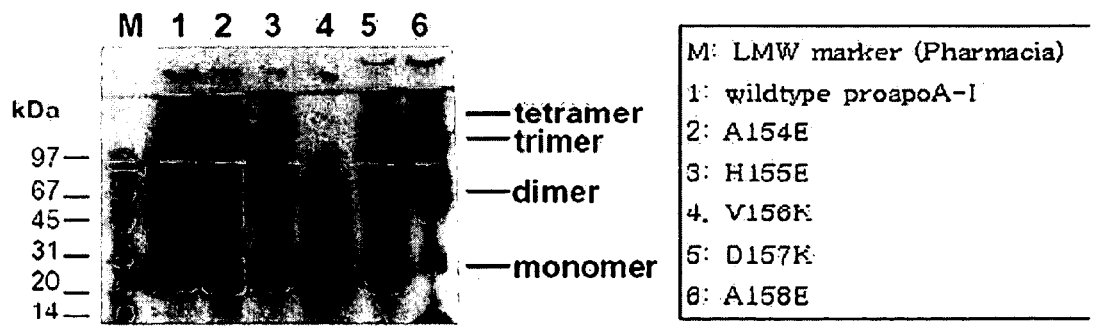
Figure 9:
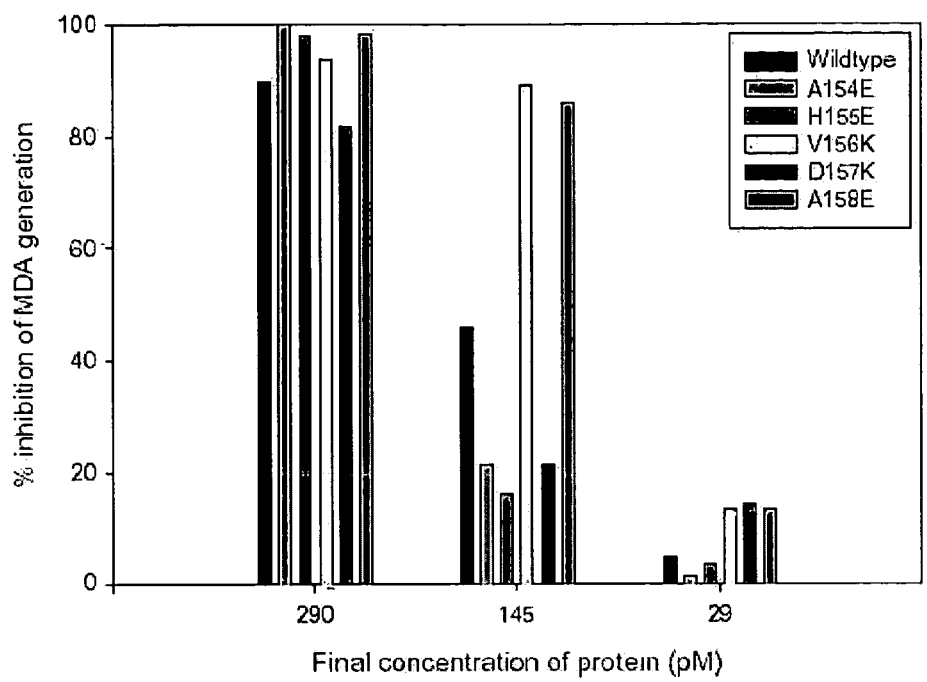
Figure 10:
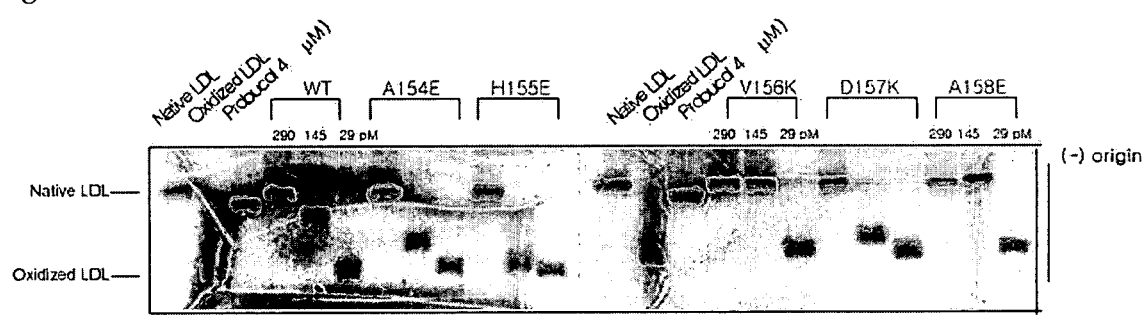
Figure 11:
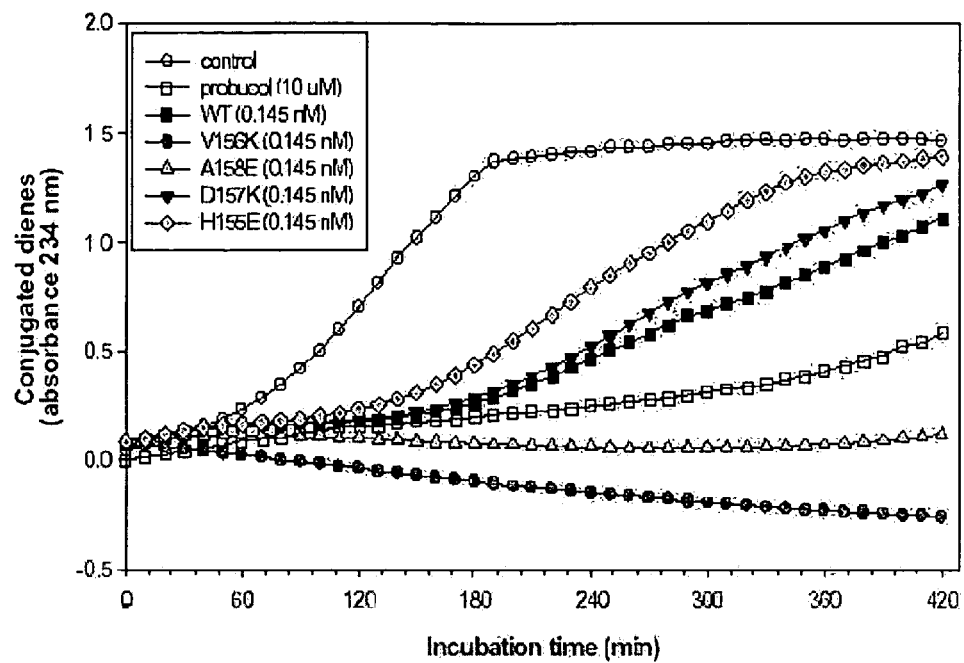
Figure 12:
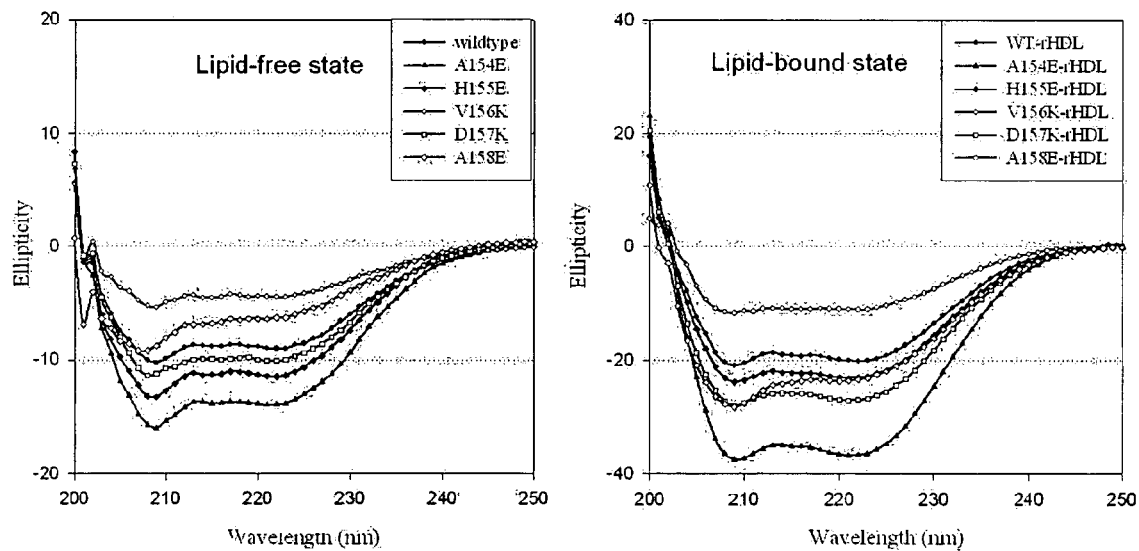
Figure 13:
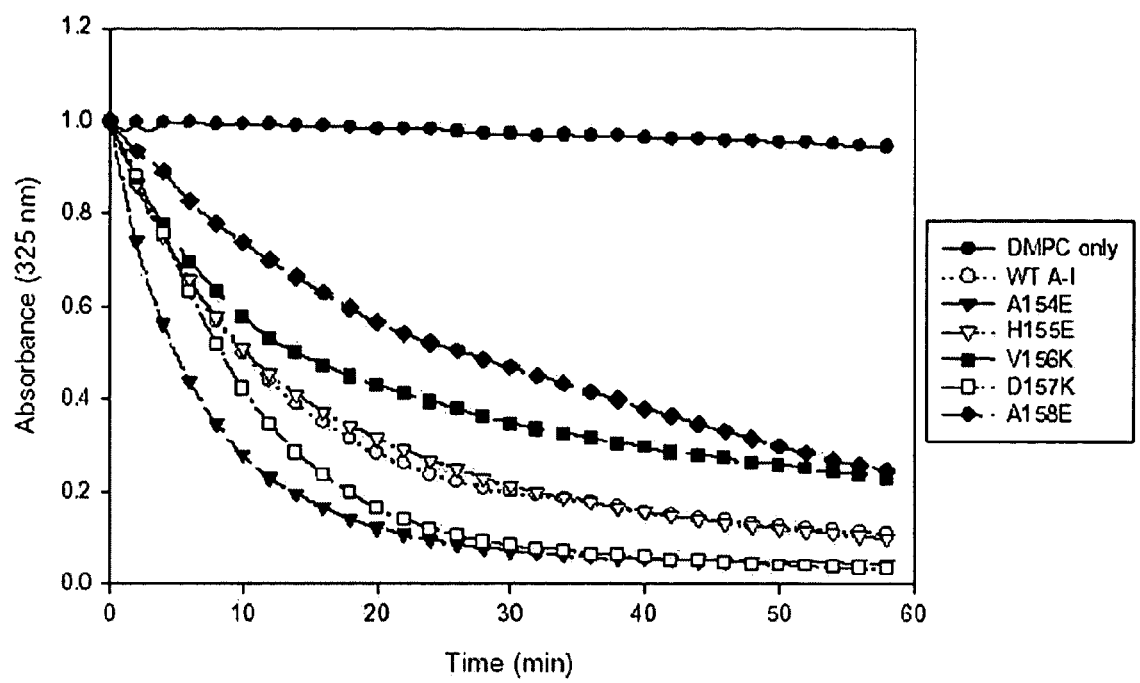
Figure 14:
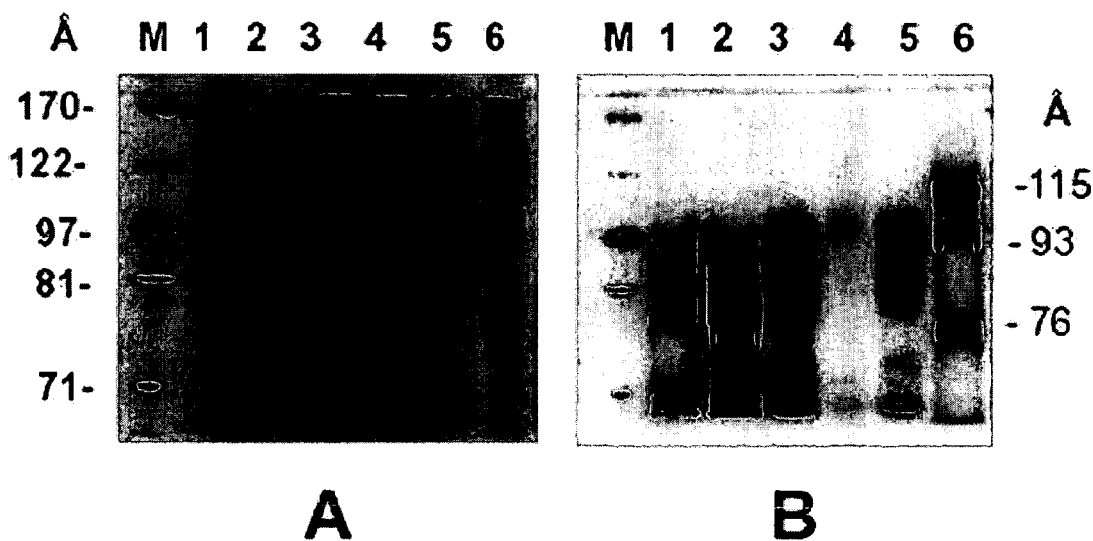
Figure 16:
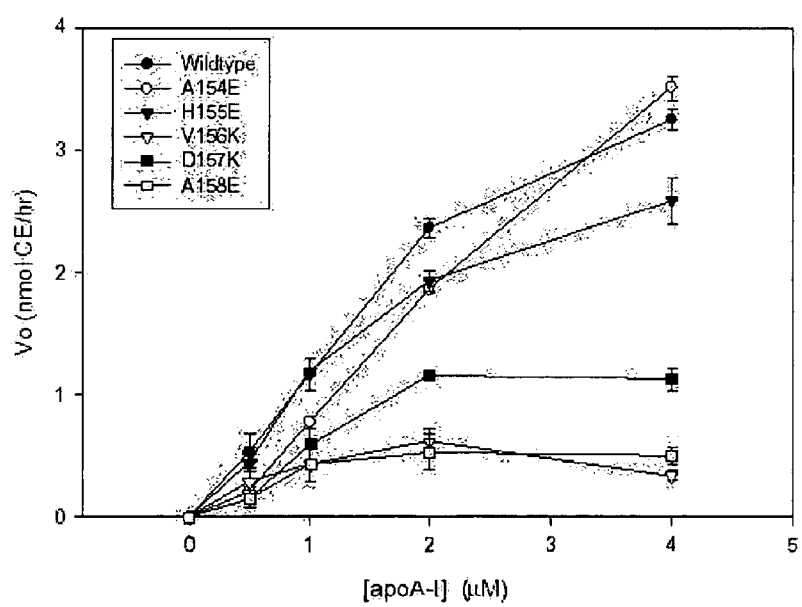
Figure 17:
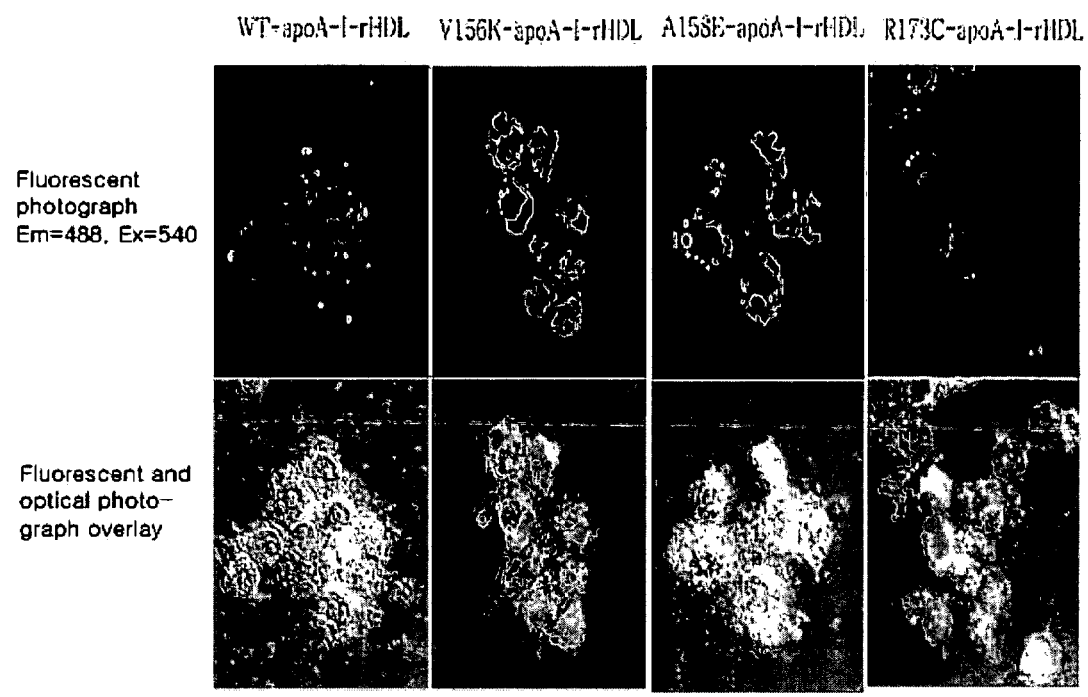
Figure 18:
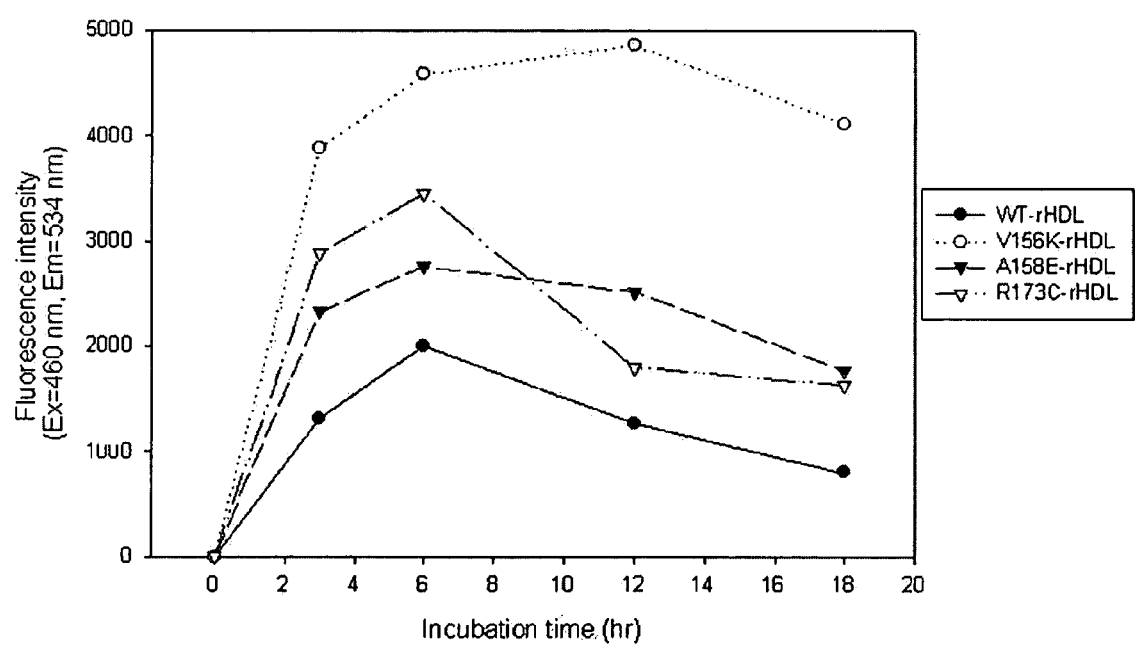
Figure 19:
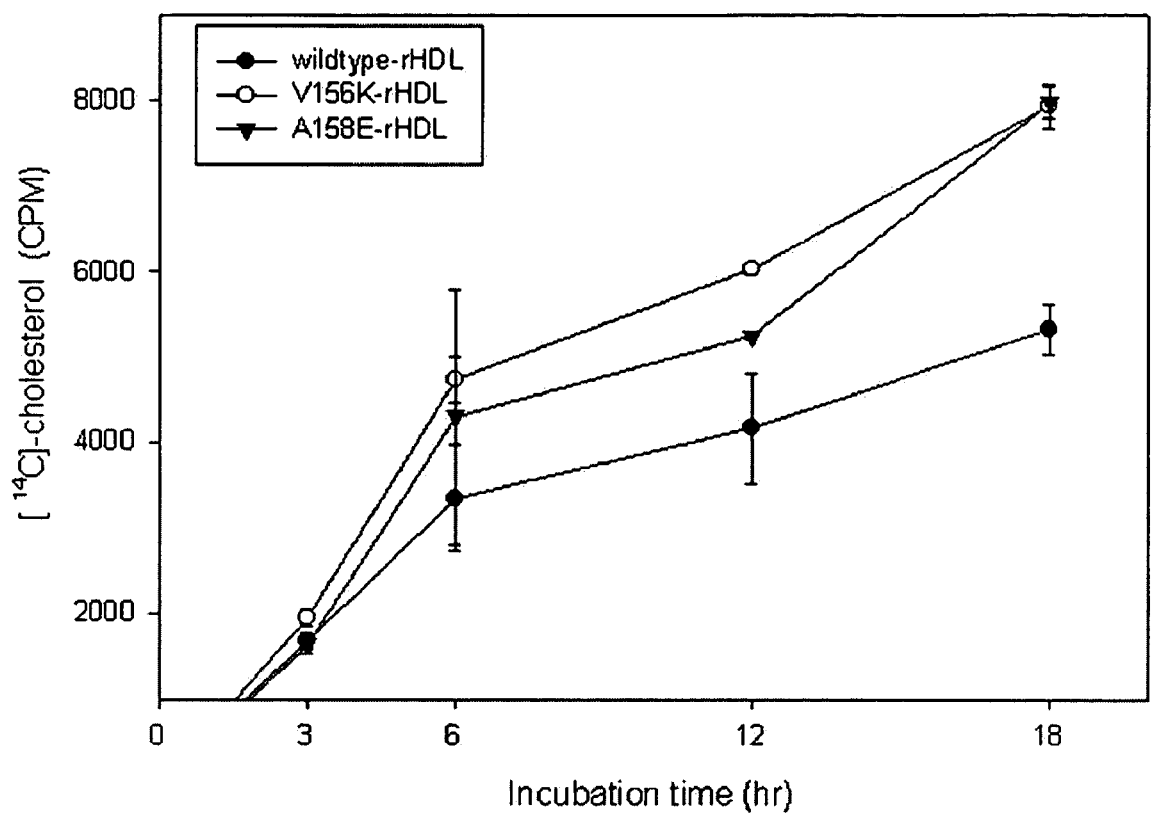
Figure 20:
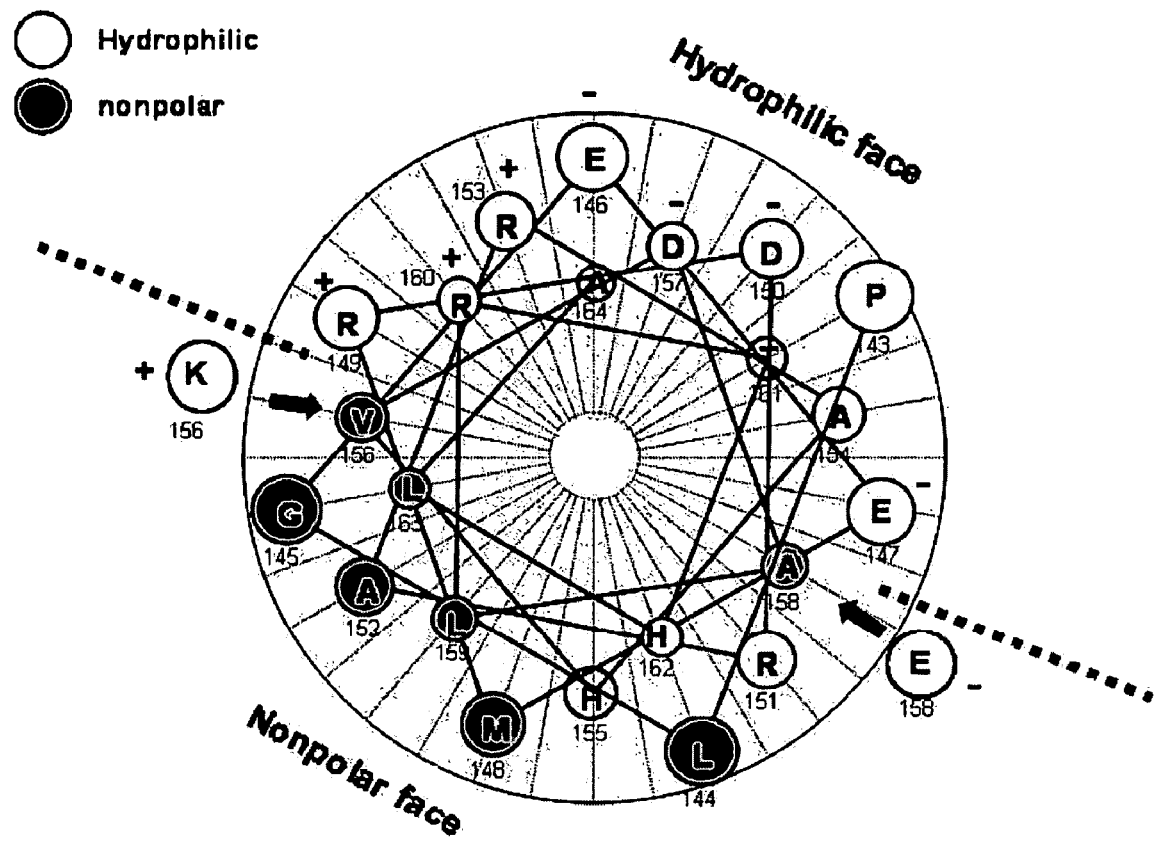

FIG. 6 shows the result of treating a fusion protein(33 kDa) with enterokinase to remove a poly(His)$_6$-tag therefrom;

FIG. 7 shows the result of analyzing the purified proapoA-I and mutants thereof with 20% SDS-PAGE;

FIG. 8 shows the proapoA-I and mutants thereof after a cross-linking reaction under a lipid-free condition;

FIG. 9 shows the result of measuring LDL-antioxidant activities of the proapoA-I and mutants thereof according to TBARS(thiobarbituric acid reactive substances) method;

FIG. 10 shows the result of comparing LDL-antioxidant activities of the proapoA-I and mutants thereof with agarose gel electrophoresis;

FIG. 11 shows the result of comparing LDL-antioxidant activities of the proapoA-I and mutants thereof by monitoring the formation of a conjugated diene;

FIG. 12 shows the results of measuring the ratios of alpha-helix in the proapoA-I and mutants thereof according to a circular dichroism spectroscopy method;

FIG. 13 shows the result of comparing activities of the proapoA-I and mutants thereof to react with dimyristoyl phosphatidyl choline(DMPC);

FIG. 14 shows the result of reconstituting the proapoA-I and mutants thereof into rHDL using POPC A: POPC:chloesterol:proapoA-I=95:5:1, B: POPC:cholesterol:proapoA-I=40:0:1;

FIG. 15A-B shows the results of analyzing a multimerization tendency through a cross-linking reaction at a POPC-rHDL condition;

FIG. 16 shows the result of comparing LCAT activities of the proapoA-I and mutants thereof at a POPC-rHDL condition;

FIG. 17 shows the results of measuring activities of the proapoA-I and mutants thereof(V156K, A158E) for delivering cholesterol to hepatocytes(Hep G2) at a POPC-rHDL condition with a confocal microscope;

FIG. 18 shows the result of measuring activities of the proapoA-I and mutants thereof(V156K, A158E) for delivering cholesterol to hepatocytes(Hep G2) at a POPC-rHDL condition with Victor2 optical microplate reader;

FIG. 19 shows the result of measuring activities of the proapoA-I and mutants thereof(V156K, A158E) for delivering cholesterol to hepatocytes(Hep G2) at a POPC-rHDL condition with a scintillation counter; and FIG. 20 shows the result of analysis of the sixth helix domain of the wild-type apoA-I.

DETAILED DESCRIPTION OF THE INVENTION

The present invention provides a proapoA-I mutant, a proapolipoprotein mutant comprising Ala-His-Phe-Trp-Gln-Gln at the amino terminal of apolipoprotein(apoA-I) wherein a mutation is introduced in the proapolipoprotein (proapoA-) at any one of the $154^{th}$, $155^{th}$, $156^{th}$, $157^{th}$ and $158^{th}$ amino acids of the apoA-I.

Hereinafter, the present invention is described in detail.

The proapoA-I mutant of the present invention comprising a mutation at any of the $154^{th}$, $155^{th}$, $156^{th}$, $157^{th}$ and $158^{th}$ amino acid positions in the proapoA-I containing the sequence of Ala-His-Phe-Trp-Gln-Gln at the amino terminal of apoA-I is obtained from the result of analyzing the secondary structure of the sixth helix domain corresponding to the $143^{rd}$-$164^{th}$ amino acids of the apoA-I and not originated from nature as described in the previously reported prior arts and patents.

Preferred embodiments of proapoA-I mutants of the present invention are as follows:

A154E: the $154^{th}$ amino acid(Ala) of apoA-I is replaced by glutamic acid(SEQ ID No: 19);

H155E: the $155^{th}$ amino acid(His) of apoA-I is replaced by glutamic acid(SEQ ID No: 20);

V156K: the $156^{th}$ amino aicd(Val) of apoA-I is replaced by lysine(SEQ ID No: 21);

D157K: the $157^{th}$ amino acid(Asp) of apoA-I is replaced by lysine(SEQ ID No: 22); and A158E: the $158^{th}$ amino acid(Ala) of apoA-I is replaced by glutamic acid(SEQ ID No: 23).

In particular, V156K and A158E among five mutants described above show higher activities for prevention and treatment of atherosclerosis or hyperlipidemia than a wild-type and apoA-I Milano(R173C).

Further, the present invention comprises cDNA encoding the proapoA-I mutant, a recombinant vector containing the same, and a cell transformed using the vector.

As a result of assessing the antioxidant effects of the proapoA-I mutants of the present invention on LDL(low density lipoprotein) according to thiobarbituric acid reactive substance(TBARS) method, V156K and A158E show high antioxidant effects. Further, the results for measuring their activities for delivering cholesterol to hepatocytes with a confocal microscope, an optical microplate reader, and a scintillation counter suggest that V156K and A158E mutants exhibit good delivering activities.

Therefore, the proapoA-I mutants of the present invention can be effectively used for preventing or treating atherosclerosis or hyperlipidemia by utilizing itself or the form of a reconstituted high density lipoprotein(rHDL) comprising the same as an effective ingredient.

The pharmaceutical composition for oral administration of the present invention comprises the proapoA-I mutant in combination with a pharmaceutically acceptable carrier. The pharmaceutical composition may be formulated into various pharmaceutical preparations for oral administration, e.g., a tablets, troches, lozenges, soluble or oily suspensions, powder or granules, emulsions, hard or soft capsules, syrups or elixirs, in accordance with any of the conventional procedure. Tablets, coated tablets, capsules, pills and granules can further contain binders such as lactose, saccharose, sorbitol, mannitol, starch, amylopectin, cellulose and gelatin; excipients such as dicalcium phosphate; disintegrants such as corn starch and sweet potato starch; and lubricants such as calcium stearate, magnesium stearate, stearylfumaric acid and polyethyleneglycol wax. Tablets may further contain liquid carriers such as fatty oil besides the above.

Further, the pharmaceutical composition may be parentally administered, and the parental administration may be obtained via subcutaneous injection, intravenous injection, intramuscular injection or chest injection. The pharmaceutical composition may be formulated into a pharmaceutical preparation for parental administration by a conventional method. For example, the parental preparation may be prepared by dissolving the proapoA-I mutant with a stabilizer or a buffering agent in water to prepare a solution or a suspension and filling the solution or the suspension in an ample or a vial.

For the purpose of a clinical administration, a typical daily dose of the proapoA-I mutant may range from 15 to 45 mg/kg body weight, preferably from 45 to 80 mg/kg body weight and can be administrated in a single dose or in several divided doses. However, it can be changed into a higher or lower daily dose with the effective ingredient depending on a certain disease. Further, it should be understood that the amount of the effective ingredient actually administrated to a certain patient ought to be determined in light of various relevant factors including the kind of effective compound administered, the body weight, age, sex, health condition, diet and excretion rate of the individual patient, the chosen route of administration, the combination of drugs and the severities of a patient's symptoms.

The following Examples are given for the purpose of illustration only, and they should not be construed as limiting the scope of the present invention.

EXAMPLE 1

Nucleotide Sequence of ProapoA-I

Since apoA-I consisting of 243 amino acids(SEQ ID No: 1)(FIG. 1) showed a low expression yield in a host expression system and was unstable during the purification, a gene encoding a wild-type(WT) proapoA-I(SEQ ID No: 2, 258 amino acids)(FIG. 1) further containing 15 amino acids (including the sequence of Ala-His-Phe-Trp-Gln-Gln) at the amino terminal of the WT apoA-I was inserted into vector pET30a(Novagen, USA), to obtain expression vector pET30a-proapoA-I expressing human apoA-I(Cho and Jonas, 2000, *J. Biol. Chem.* 275: 26821-26827). Since the proapoA-I expressed from the vector contained a $(His)_8$-tag(5 kDa) at its amino terminal, it was found that a total protein size thereof corresponded to 32-33 kDa on SDS-PAGE.

EXAMPLE 2

Cloning of ProapoA-I Template DNA

Figure 3:
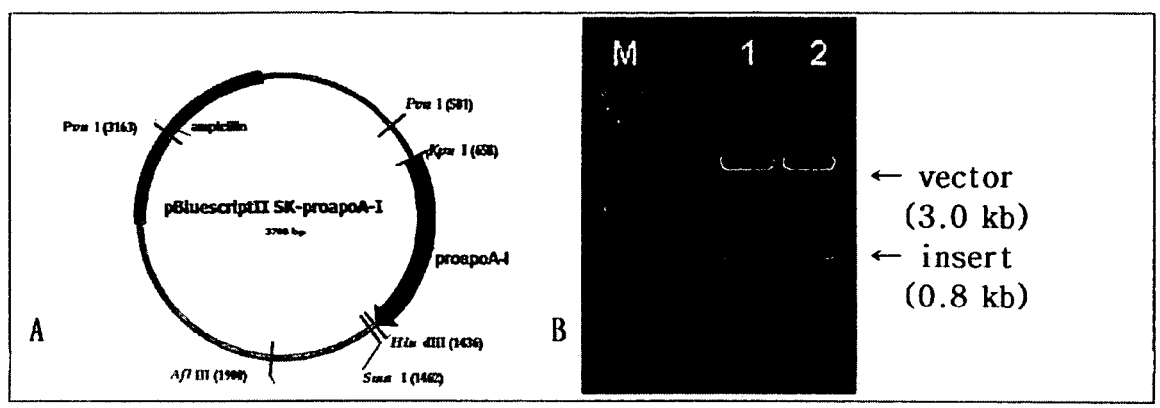
FIG. 3A shows a restriction map of a proapoA-I expression vector, pBlueScriptII-SK-proapoA-I.
FIG. 3B shows cDNA bands of the expression vector, pBlueScriptII-SK-proapoA-I, and an insert(wild type proapoA-I)

The WT proapoA-I cDNA according to the present invention was fused with a $(His)_6$-tag at its amino terminal and cloned at vector pET30a(Novagen, USA). However, since the vector's size was about 6.2 kb and, it was unsuitable for using as a PCR template for producing cDNA encoding a mutant. Therefore, the expression vector pET30a-proapoA-I was treated with KpnI and HindIII to obtain a cDNA insert encoding the proapoA-I(795 bp) (FIG. 2, SEQ ID No: 3), and the insert was cloned into vector pBlueScriptII SK(+) (Stratagene), to obtain vector pBlueScriptII SK-proapoA-I. *E. coli* DH5a was transformed with the resulting vector pBlueScriptII SK-proapoA-I(FIG. 3) to obtain an *E. coli* transformant designated DH5a/pBlueScriptII SK-proapoA-I which was deposited at Korean Collection for Type Cultures (Address: #52, Oun-dong, Yusong-ku, Taejon 305-333, Republic of Korea) on Jun. 7, 2004 under the accession number of KCTC 10651BP, in accordance with the terms of the Budapest Treaty on the International Recognition of the Deposit of Microorganisms for the Purposes of Patent Procedure.

EXAMPLE 3

Production of ProapoA-I Mutants and Construction of Expression Vectors Thereof In order to produce five proapoA-I mutants(A154E, H155E, V156K, D157K and A158E) according to the present invention, each mutant cDNA was amplified by PCR using Pfu DNA polymerase. At this time, PCR was carried out using the expression vector pBlueScriptII SK-proapoA-I prepared in Example 2 as a template and synthetic primer pairs described in Table 2 with QuickChange site directed mutagenesis kit(Stratagene).

well or not was confirmed by comparing the size of an expected fragment with that of a band observed in electrophoresis.

TABLE 3

| site Mutants | Afl III (site#) | Pvu I (site#) | Sma I (site#) | band number (size) |
|---|---|---|---|---|
| WT | x (1900) | o (3163, 501) | x (1462) | Pvu I: 2662 bp + 1046 bp |
| A154E | o (1164, 1900) | | | 2 (2962 bp, 746 bp) |
| H155E | | o (501, 1152, 3163) | | 3 (2011 bp, 1046 bp, 651 bp) |
| V156K | | | o (1159. 1462) | 2 (3405 bp, 303 bp) |
| D157K | o (1164, 1900) | | | 2 (2962 bp, 746 bp) |
| A158E | o (1164, 1900) | | | 2 (2962 bp, 746 bp) |

The size of apoA-I mutant DNA amplified by PCR was about 0.8 kb. In order to select an exact mutant from the clones, A154E, D157K and A158E were respectively digested with AflIII, H155E with PvuI, and V156K with SmaI(Table 3 and FIG. 4). As seen in FIG. 4, the mutants

TABLE 2

```
WILD TYPE  5'-ATGCGCGACCGCGCGCGCGCCCATGTGGACGCGCTCCGGACGCATCTGGCC-3'
                           Ala His  Val Asp Ala

A154E      5'-ATGCGCGACCGCGCGCGCGAACATGTGGACGCGCTC-3'           (sense: SEQ ID No:4)

5'-GAGCGCGTCCACATGTTCGCGCGCGCGGTCGCGCAT-3'          (antisense: SEQ ID No:5)

H155E      5'-CGCGATCGCGCGCGAGCGGAAGTCGACGCCCTCCGG-3'           (sense: SEQ ID No:6)

5'-CCGGAGGGCGTCGACTTCCGCTCGCGCGATCGCG-3'             (antisense: SEQ ID No:7)

V156K      5'-GACCGCGCCCGGGCCCATAAGGACGCGCTCCGGACG-3'           (sense: SEQ ID No:8)

5'-CGTCCGGAGCGCGTCCTTATGGGCCCGGGCGCGGTC-3'           (antisense: SEQ ID No:9)

D157K      5'-CGCGCGCGCGCACACGTGAAGGCGCTCCGGACGCAT-3'           (sense: SEQ ID No:10)

5'-ATGCGTCCGGAGCGCCTTCACGTGTGCGCGCGCGCG-3'           (antisense: SEQ ID No:11)

A158E      5'-GCGCGCGCACACGTGGACGAACTCCGGACGCACCTG-3'           (sense: SEQ ID No:12)

5'-CAGGTGCGTCCGGAGTTCGTCCACGTGTGCGCGCGC-3'           (antisense: SEQ ID No:13)
```

As seen in Table 2, each primer was designed to have 36-mer oligonucleotides. After the PCR reaction, the PCR products were treated with DpnI to remove all the unreacted template DNA(parental DNA), and clones having a mutation were primarily selected therefrom by restriction enzyme treatment. At this time, each primer was designed to comprise a recognition site of a specific restriction enzyme as described in Table 3, which results in minimizing the costs and time for confirming the all PCR products with DNA sequencing.

Table 3 shows the results of confirming the production of proapoA-I mutants with restriction enzyme treatment, wherein o means that a corresponding restriction enzyme acts on the mutant and x means that it does not. Further, whether a mutation for the production of a mutant occurs having a mutation at a target site were selected from the clones by restriction enzyme treatment as illustrated in Table 3. In case of A154E(A), D157K(D) and A158E(E), 2962- and 746-bp of two bands were observed by the digestion with AflIII. Three bands(2011-, 1046- and 651-bp) were observed in H155E(B) by the digestion with PvuI, while V156K(C) showed two bands(3405- and 303-bp) by the digestion with SmaI. These results suggest that the five clones selected above are mutants in which one amino acid at a certain position is replaced by other amino acid.

The mutant clones primarily selected by the restriction enzyme treatment were subjected to DNA sequencing to confirm an exact mutation site and a full-length cDNA sequence thereof. The clones thus confirmed were subcloned to vector pET30a(+) together with the WT apoA-I, and the resulting vector was transformed into *E. coli*(BL21) competent cell. The *E. coli* transformant was selected on kanamycin-LB medium and digested with KpnI and HindIII, to confirm the cloning of the insert gene as shown in FIG. 4.

EXAMPLE 4

Expression and Production of a Wild-type and Mutants From *E. coli*

Figure 5:
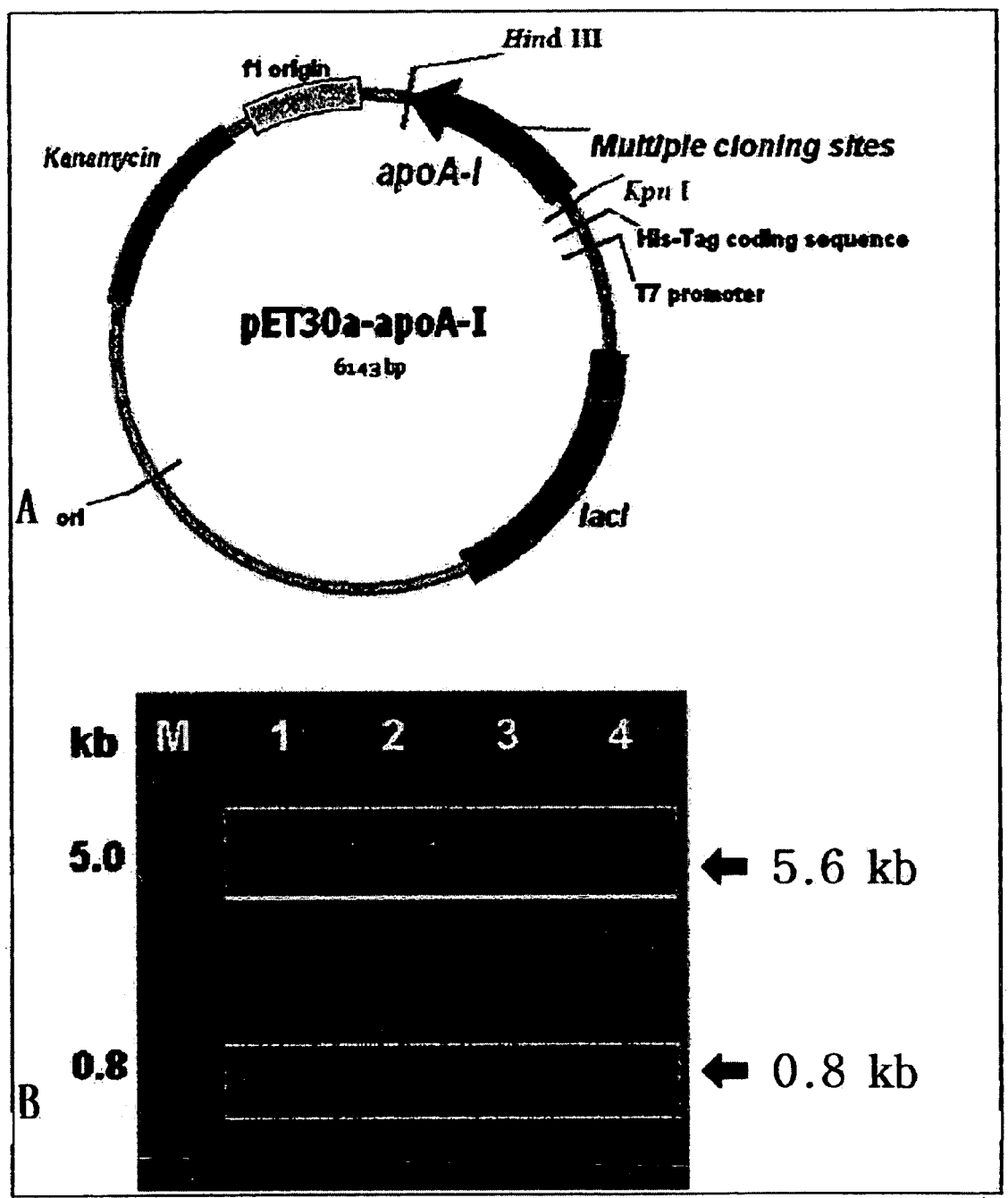

Each mutant cDNA obtained in Example 3 was subjected to DNA sequencing to analyze a mutation site and a full-length amino acid sequence thereof. The mutant cDNAs confirmed by DNA sequencing were cloned into vector pET30a(+) and the resulting vectors were treated with KpnI and HindIII to confirm the size of insert DNA, respectively (FIG. 5). Each expression vector was transformed into *E. coli* BL21 by heat shock treatment.

The *E. coli* transformant designated BL21/pET30a(+)-V156K-proapoA-I which was deposited at Korean Collection for Type Cultures(Address: #52, Oun-dong, Yusong-ku, Taejon 305-333, Republic of Korea) on Jun. 7, 2004 under the accession number of KCTC 10652BP, in accordance with the terms of the Budapest Treaty on the International Recognition of the Deposit of Microorganisms for the Purposes of Patent Procedure.

Further, the *E. coli* transformant designated BL21/pET30a(+)-A158E-proapoA-I which was deposited at Korean Collection for Type Cultures(Address: #52, Oun-dong, Yusong-ku, Taejon 305-333, Republic of Korea) on Jun. 7, 2004 under the accession number of KCTC 10653BP, in accordance with the terms of the Budapest Treaty on the International Recognition of the Deposit of Microorganisms for the Purposes of Patent Procedure.

The *E. coli* transformant BL21/pET30a-proapoA-I mutant clones were cultured in 250 mL of LB medium supplemented with kanamycin, respectively, and when $OD_{600}$ was reached 0.7 or more, the culture solution was treated with IPTG(isopropyl-β-D-thiogalactoside) at a final concentration of 1 mM to induce the expression of a target protein. After examined the optimal time for inducing the maximum expression of a target protein, the cells were further cultured for the corresponding period of time(1-4 hrs). The culture solution was centrifuged at 6,000×g to harvest a cell pellet, and the cell pellet was subjected to sonication to disrupt a cell membrane and elute a total protein. Then, the reactant was subjected to solubilization in a cold buffer(4° C.) containing 6 M Gnd-HCl for 18 hrs or more, and the protein solution thus obtained was loaded onto Ni-NTA(Qiagen) column chromatography, to purify only the apoA-I mutant. The protein eluted from the $Ni^{2+}$-column was dialyzed into TBS buffer(10 mM Tris/140 mM NaCl/1 mM EDTA, pH 8.0) to remove imidazole and quantified. As a result, about 5-10 mg of the protein was produced from the expression and purification procedures of all the mutants. As a result of 12% SDS-PAGE, as can be seen in FIG. 6, they showed 95% or more purity and detected all as a protein band having a molecular weight of 33 kDa which corresponds to the molecular weight of a fusion protein of 28 kDa protein and 5 kDa His-tag(Lanes 1 and 6).

The amino acid sequences of the mutants synthesized above were shown as SEQ ID Nos: 19 to 23, as follows.

SEQ ID No: 19 is Poly(His)$_6$-proapoA-I-A154E: the 154$^{th}$ amino acid(Ala) of apoA-I is replaced by glutamic acid.

SEQ ID No: 20 is Poly(His)$_6$-proapoA-I-H155E: the 155$^{th}$ amino acid(His) of apoA-I is replaced by glutamic acid.

SEQ ID No: 21 is Poly(His)$_6$-proapoA-I-V156K: the 156$^{th}$ amino aicd(Val) of apoA-I is replaced by lysine.

SEQ ID No: 22 is Poly(His)$_6$-proapoA-I-D157K: the 157$^{th}$ amino acid(Asp) of apoA-I is replaced by lysine.

SEQ ID No: 23 is Poly(His)$_6$-proapoA-I-A158E: the 158$^{th}$ amino acid(Ala) of apoA-I is replaced by glutamic acid.

EXAMPLE 5

Re-Synthesis of Phospholipid of ProapoA-I Mutants and Removal of a His-tag

In order to prevent a non-specific protein digestion which may occur during the entrokinase treatment for the removal of 5 kDa poly(his)$_6$-tag and protect an original form of the proapoA-I, the mutant proteins were synthesized into reconstituted HDL(rHDL). Egg phosphatidylcholine(EPC) was mixed with cholesterol at a molar ratio of phospholipid:cholesterol to be 95:5:1 and completely dried under nitrogen atmosphere. The dried reactant was dissolved in TBS buffer to form a liposome, sodium cholate(30 mg/mL) and each mutant protein was added thereto, and then reacted at 4° C. for 1 hr. The reaction mixture was dialyzed into TBS buffer for 24 hrs to induce the formation of rHDL. The rHDL mixture thus obtained was treated with enterokinase(1/1200, wt/wt, Roche) and kept at room temperature. In order to assess a proper reaction condition and time, samples were collected from the mixture before, and at 12, 24, 36 and 43 hrs after the reaction, and subjected to SDS-PAGE. As a result, as shown in FIG. 6, it has been found that only the His-tag was selectively removed with the lapse of reaction time and the amount of 28 kDa proapoA-I proteins increased up to 43 hrs after the reaction.

EXAMPLE 6

Removal of Lipid From ProapoA-I Mutants and Protein Purification

After the treatment with enterokinase, the protein solution was mixed with 5-volume of a mixture of ethanol and diethyl ether(3/2, v/v) and stirred for 1 hr to remove lipid from the mutant protein. The above step was repeated at least two times. The resulting solution was extracted with a mixture of hexane and isopropanol(3/2, v/v) to remove only the phospholipid, and subjected to $Ni^{2+}$-NTA-column chromatography to purify 28 kDa of the proapoA-I protein having no His-tag from the mixture of 5 kDa of His-tag and 33 kDa of His-tag fusion proteins. The purified protein was analyzed with SDS-PAGE, and the results are shown in FIG. 7.

EXAMPLE 7

Cross-linking and Multimerization Pattern Analysis of of ProapoA-I Mutants

The WT proapoA-I shows high intermolecular interaction and self-association tendency and thus can be easily corsslinked by a crosslinker. Each mutant was reacted with BS3(Bis-sulfosuccinimidyl substrate) having a length of 11.4 Å at a concentration of 0.05, 0.1, 1 or 2 mg/mL, and the products were loaded onto 8-25% SDS-PAGE(Pharmacia Phast System) to compare self-association efficiencies of a dimer, trimer and tetramer, and the results are shown in FIG. 8.

Most of the WT proapoA-I and mutants mainly existed as a monomer in a lipid-free state and they showed a multimerization pattern comprising dimers, trimers and tetramers, while more than 90% of V156K existed only as monomers and its trimers and tetramers were not detected. Further, A158E showed a very low percentage of monomers and the ratio of dimers thereof was higher than 80%. These results suggest that V156K(Lane 4) shows a distinct tendency that it is not involved in a cross-linking reaction, whereas most molecules of A158E(Lane 6) participate in a cross-linking reaction.

EXAMPLE 8

Analysis for Antioxidant Activities of ProapoA-I Mutants on LDL

Since it has been reported that the inhibition of LDL oxidation is a key factor for prevention and treatment of artheriosclerosis, antioxidant activities of the proapoA-I and mutants thereof were analyzed as follows. LDL(0.12 mg/mL) purely purified from human plasma by centrifugation was mixed with $Cu^{2+}$ as an oxidant at a final concentration of 5 μM to induce oxidation, and each of the proapoA-I and mutants thereof was added thereto as an antioxidant. The reaction mixture was subjected to TBA (thiobarbituric acid) reaction for a certain period of time. The antioxidant efficiencies of proapoA-I and mutants thereof were determined by measuring the amount of malonedialdehyde(MDA) generated after the reaction. Here, the concentration of LDL was 0.19 μM, and Probucol, a commercially available antioxidant, was used as a positive control at a concentration of 4 μM. The reaction mixture was prepared by mixing 10 μL of LDL, a proper amount of the proapoA-I-mutant corresponding to $CuSO_4$ concentration and PBS(phosphate buffer saline) in a final volume of 250 μL. The reaction mixture was reacted at 37° C. for 4 hrs, and 20% TCA(trichloroacetic acid) was added thereto to stop the reaction. After the treatment of TCA, 1 mL of 0.67% TBA was added to the reaction mixture, completely mixed, and heated to 95° C. for 15 min. At this time, there was a change in the reaction mixture's color due to the formation of an oxidized product. The reaction mixture was centrifuged to separate a supernatant by precipitating solid substances, and the antioxidant activity of the proapoA-I mutant was analyzed by measuring the amount of MDA formed in the supernatant with a spectrophotometer(Agilent Technologies, Germany).

As a result, the WT proapoA-I and their mutants thereof according to the present invention showed high antioxidant activities at a final concentration of 290 pM, and, in particular, V156K and A158E1 showed superior antioxidant activities to the WT proapoA-I and other mutants at a final concentration of 145 pM. However, their antioxidant activities were largely lost at a final concentration of 29 pM(FIG. 9).

In order to confirm the results of FIG. 9 analyzed by the TBARS method, some LDL reactant was taken from the reaction mixture and subjected to electrophoresis on a 0.7% agarose gel. As a result of conducting the gel electrophoresis of native LDL before the reaction and oxidized LDL after the reaction simultaneously based on the principle that the more LDL is oxidized, the faster LDL migrates downward, it has been found that LDL added with 290 pM of the mutant protein is located at the same position as the native LDL before the reaction and at an upper position rather than LDL added with a positive control(4 μM probucol), which means that the oxidation occurs less. In particular, LDL added with 145 pM of V156K or A158E was located at the same position as the native LDL before the reaction. These results demonstrate that V156K and A158E showed more powerful LDL-antioxidant activities than the WT proapoA-I and other mutants and coincide with the TBARS results(FIG. 10).

To further confirm the above results, $Cu^{2+}$ was added to the reaction mixture at a final concentration of 5 μM to induce oxidation of LDL, and the concentration of an oxide, a conjugated diene, produced by the above oxidation reaction was compared with that of the oxide produced when the reaction mixture was treated with 145 pM of the WT proapoA-I or mutants, respectively. The amount of conjugated diene thus produced was quantified by comparing the absorbance at 234 nm of ultraviolet. As can be seen in FIG. 11, V156K and A158E completely inhibited the formation of conjugated diene and showed higher LDL-inhibitory activities than a positive control(10 μM probucol). H155E and D157K showed lower LDL-antioxidant activities than the WT proapoA-I and further lower than a positive control.

EXAMPLE 9

Analysis for Secondary Structures of ProapoA-I Mutants Using Circular Dichroism Spectroscopy In order to analyze the secondary structures of the WT proapoA-I and mutants thereof, compositions of their a-helix were measured with a circular dichroism spectroscopy method using J-700 spectropolarimeter(Jasco, Tokyo, Japan). The level of helicity of the proapoA-I mutant was determined by scanning a spectrum ranging from 250 to 190 nm at 10.1 nm of band width and 4 sec of response time using a quartz circular dichroism cuvette having a pathlength of 0.1 cm, measuring ellipticity at 222 nm, and calculating an average molecular weight of the mutant protein therefrom, to determine the amount of α-helix(Chen et al., 972, *Biochemistry* 11:4120-4131). To prevent the formation of self-association between the proteins, the proteins and the reconstructed HDL(rHDL) were diluted with distilled water to a concentration of 0.07 mg/mL and 0.1 mg/mL, respectively. The scanning procedure was repeated four times and the a-helicity ratio was calculated by using an average value obtained therefrom. As a result, the spectrum as described in FIG. 12 was obtained and all the proteins showed a typical pattern of a-helix protein representing the minimum value at 208 and 222 nm in both the lipid-free and lipid-bound states. Further, they showed lower ellipticities in the lipid-bound state, which means that the amount of α-helix increases due to the coupling with lipid. The unique feature in the lipid-free state was that ellipticities of V156K and A158E were lower than that of the WT proapoA-I, and A154E, H155E and D157K showed higher ellipticities than the WT proapoA-I. In the lipid-bound state, only V156K showed higher ellipticity than the WT proapoA-I, and the rest of the mutants, i.e., A154E, H155E, D157K and A158E, showed lower ellipticity than that. These results were used for calculating the amount of α-helix and showed the α-helicity for each protein as described in Table 4. While the WT proapoA-I showed 54±4% of α-helicity in the lipid-bound state, V156K and A158E showed 40±3% and 49±3% of α-helicities, respectively, which were lower than that of the WT proapoA-I, and A154E, H155E and D157K showed higher α-helicities than the WT proapoA-I. Among them, D157K showed the highest α-helicity of 63±5%. In the lipid-bound state, the WT proapoA-I, A154E and D157K showed similar α-helicities ranging from 74-76%, but V156K and A158E showed lower α-helicities of around 65%, which suggests that the tendency to increase α-helicity during the lipid coupling reaction is not big as much as the amount of the WT proapoA-I.

EXAMPLE 10

Analysis of Tryptophan Fluorescence Activities of ProapoA-I Mutants

Wavelengths of maximum fluorescence(WMF) of tryptophan residues existed in the WT proapoA-I and proapoA-I-mutants were measured with LS50B spectrophotometer (Perkin-Elmer, Norwalk, Conn.) using a quartz supracil cuvette(Fisher Scientific, Pittsburg, Pa.) having a pathlength of 1 cm. At this time, each sample was diluted with distilled water to a concentration ranging from 0.07 to 0.1 mg/mL. The recorded data were calculated by averaging the measured values obtained from four times of scanning and analyzed with WinLab software package 4.00(Perkin-Elmer). In order to inhibit tyrosine fluorescence excitation in the protein sample, each sample was activated at 295 nm(Ex=295 nm), and measured its emission spectrum at a wavelength ranging from 305 to 400 nm. All the spectra were recorded at room temperature. As can be seen in Table 4, while the WT proapoA-I and most of the mutants showed WMF ranging from 336 to 338 nm in the lipid-free state, WMF of A158E mutant was 340 nm. These results suggest that tryptophan residues of A158E are more exposed to the aqueous solution due to the difference in its protein structure than the WT proapoA-I and other mutants. The WT proapoA-I synthesized in the form of POPC-rHDL showed a tendency to decrease WMF by 2 to 3 nm than the lipid-free state as converted into the lipid-bound state, while the WT proapoA-I and other mutants showed WMF ranging from 334 to 336 nm. However, V156K and A158E showed WMF at 337 nm, which means that although these proteins undergo the lipid coupling reaction, the level of exposing their tryptophan residues is unchanged. Accordingly, these results suggest that V156K and A158E suffer less change in their tertiary structures during the lipid coupling reaction than other mutants, and coincided with the results obtained in Example 9 that the tendency to increase a-helicities of V156K and A158E during the lipid coupling reaction is not as big as that of the WT proapoA-I.

EXAMPLE 11

Comparison of DMPC Phospholipid Binding Affinities of ProapoA-I Mutants

Binding affinities of the proapoA-I mutants for lipids were measured by using dimyristoyl phosphatidyl choline(DMPC) according to the method described by Pownall et al.(1978, *Biochemistry* 17: 1183-1188) with some modifications. Dry powder DMPC was dissolved in TBS buffer(10 mM Tris-HCl, 160 mM NaCl, 1 mM EDTA, pH 8.0) at a final concentration of 3.5 mg/mL, to prepare multilamellar liposomes. Here, a final concentration of the protein participating in the reaction was adjusted to 0.15 mg/mL, DMPC was mixed with each protein at a molar ratio of 2:1(w/w), and a total amount of the reaction mixture was restricted to 0.76 mL. After mixed well the reaction mixture, the absorbance of the reaction mixture was measured at 325 nm with UV-Visible spectrophotometer(Agilent Technologies, Waldbronn, Germany) at 24.5° C., every 2 min and the tendency to decrease turbidity of DMPC phospholipid by the protein with the lapse of reaction time was assessed by comparing the measured absorbance values.

As illustrated in FIG. 13, A158E showed the lowest binding affinity for DMPC(half-life $T_{1/2}$=26±2 min), which demonstrates that the $158^{th}$ alanine plays an important role in the phospholipid binding. A154E mutant showed higher binding affinity for phospholipid than the WT proapoA-I($T_{1/2}$=5±2 min), and the binding affinities of H155E, V156K and D157K showed similar to that of the WT proapoA-I($T_{1/2}$=12±2 min).

EXAMPLE 12

Synthesis of Reconstituted HDLs Using the Wild-Type ProapoA-I and Mutants Thereof Reconstituted HDL(rHDL) was synthesized by mixing each of the WT proapoA-I and their mutants thereof with POPC(palmitoyloleoylphosphatidylcholine) and cholesterol according to a sodium cholate dialysis method (Matz and Jonas, 1982, *J. Biol. Chem.* 257: 4535-4540). At this time, the molar ratio of phospholipid:cholesterol:mutant was 95:5:1 or 40:0:1. The synthesized rHDLs were subjected to electrophoresis using a nondenaturating 8-25% polyacrylamide gradient gel. As shown in FIG. 14, when the molar ratio was 95:5:1, rHDLs having the size of 97 Å were synthesized dominantly, but V156K and A158E were synthesized into rHDL having a relatively larger size of at least 120 Å. When the molar ratio was 40:0:1, various rHDLs having the size of 97, 78, 83, 76, 93 or 115 Å were synthesized in all the mutant proteins.

EXAMPLE 13

Cross-Linking and Multimerization Pattern Analyses of ProapoA-I Mutant-rHDLs

In order to examine how many proapoA-I molecules are existed within rHDLs synthesized in Example 11, each of rHDLs was subjected to cross-linking reaction using $BS_3$ according to the same method as described in Example 7. Further, in order to measure the amount of the proapoA-I mutant included in the synthesized rHDL and the self-association property of the proapoA-I mutant, 1 mg each of rHDLs was subjected to cross-linking reaction using $BS_3$ according to the method described by Staros(1982, *Biochemistry* 21:3950-3955). The cross-linking reactants were analyzed with SDS-PAGE.

Figure 15:
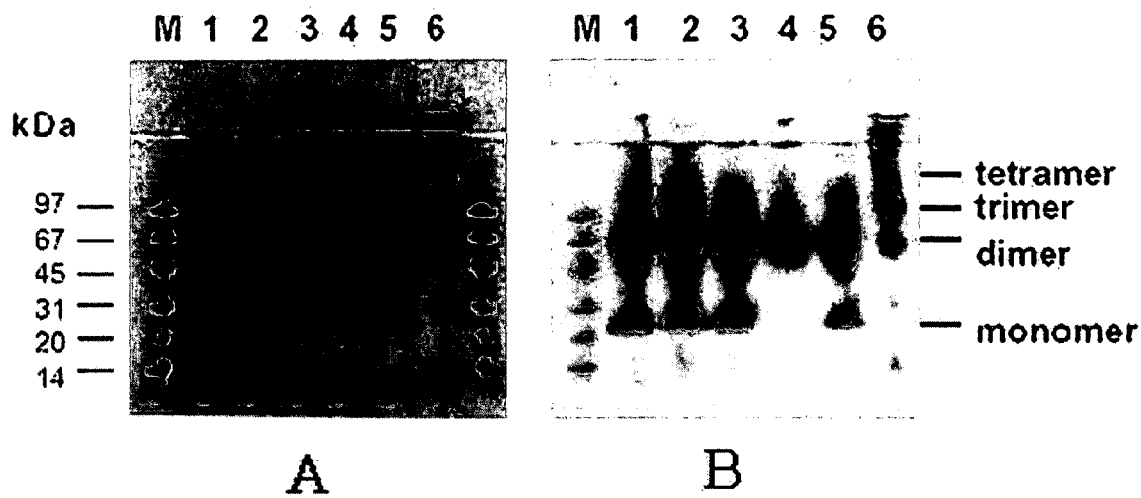

As illustrated in FIG. 15, the WT proapoA-I and other mutants except A158E showed predominantly the molecular weight of a dimeric form, which suggests that two molecules of the proapoA-I consist of one molecule of rHDL. However, since A158E showed the molecular weight of a tetramer form at the molar ratio of 95:5:1, it was understood that four molecules of the proapoA-I consist of one molecule of rHDL. When the molar ratio was 40:0:1, it was worthy of notice that all the proapoA-I molecules of V156K-rHDL take part in the cross-linking reaction to be dimerized. Further, at that time, A158E-rHDL showed three molecular bands corresponding to a dimer, a trimer and a tetramer, respectively, which suggests that a larger number of the proapoA-I molecules participate in the formation of rHDL than the WT proapoA-I and other mutants.

EXAMPLE 14

Comparison of LCAT Activation Efficiency of ProapoA-I-Mutant-rHDL

One of the important functions of apoA-I is to activate LCAT(lecitin:cholesterol acyltransferase) which is attached to HDL. rHDLs were synthesized by using the WT proapoA-I and mutants thereof with a molar ratio of phospholipid:cholesterol:proapoA-I being 95:5:1 according to the same method as described in Example 12. At this time, to facilitate the detection of cholesterol ester obtained as a product after the reaction, cholesterol labeled with radioactive isotope was used in a small amount as a molar ratio of 100:1 as compared with free cholesterol.

Each of POPC-rHDLs containing radioactive isotope-labeled cholesterol was used as a substrate and lipoprotein deficient serum(LPDS, d<1.21 bottom fraction) was used as LCAT enzyme source. 0.5 mL of a total reaction mixture was composed of POPC-synthesized rHDL(POPC:cholesterol:proapoA-I=95:5:1) including radioactive isotope-labeled cholesterol(1 μCi of [$^{14}$C]/69 μg of cholesterol/1.0 mg of apoA-I), fetal bovine serum with the removal of 4% fatty acid and 4 mM β-mercaptoethanol. After 25 μL of LPDS(5.4 mg/mL) was added to the reaction mixture, the reaction was carried out at 37° C. for 1 hr. At this time, the concentration of POPC-rHDL was regulated by varying the concentration of each proapoA-I mutant ranging from $1.0 \times 10^{-6}$ to $2.5 \times 10^{-7}$ M. After the reaction was completed, cholesterol was extracted from the reaction mixture using chloroform:methanol (2:1, v/v), and subjected to TLC(Thin layer chromatography) to separate cholesterol as a substrate and cholesterol ester as a product. Then, the radioactivity levels of each substrate and product thus separated were measured via a scintillation counter, to determine enzyme activity.

As shown in Table 4 and FIG. 16, since V156K-rHDL and A158E-rHDL showed lower activity of 2% or less compared with the WT-rHDL, it seemed that their activities for activating LCAT was almost lost. A154E and H155E showed similar activities to the WT proapoA-I, and D157K showed lower activity corresponding to 40% of the WT proapoA-I. The outlined activity($V_{max}$) and substrate affinity($K_m$) are summarized in Table 5.

It has been reported that a mimetic peptide of apoA-I Milano doesn't activate LCAT at all(Jia et al., *Biochem. Biophys. Res. Commun.* 2002, 297: 206-213). Accordingly, incapabilities of V156K and A158E for activating LCAT were similar to that of apoA-I Milano and, thus, can be effectively used for treating artheriosclerosis.

TABLE 4

| Apolipoproteins in rHDL | Apparent$^2$ $V_{max}$ | Apparent $K_m$ | Apparent $V_{max}$/Apparent $K_m$ |
|---|---|---|---|
| Wildtype-POPC-rHDL | 3.3 ± 0.3 | 0.9 ± 0.1 | 3.6 ± 0.2 |
| A154E-POPC-rHDL | 3.5 ± 0.1 | 1.0 ± 0.1 | 3.5 ± 0.1 |
| H155E-POPC-rHDL | 2.6 ± 0.5 | 1.9 ± 0.4 | 1.5 ± 0.5 |
| V156K-POPC-rHDL | 0.3 ± 0.01 | 6.2 ± 0.2 | 0.05 ± 0.01 |
| D157K-POPC-rHDL | 1.8 ± 0.1 | 2.4 ± 0.2 | 0.7 ± 0.2 |
| A158E-POPC-rHDL | 0.5 ± 0.03 | 6.0 ± 0.4 | 0.08 ± 0.03 |

EXAMPLE 15

Comparison of Activities for Delivering Cholesterol to Hepatocytes of ProapoA-I Mutant-rHDLs One of the major functions of HDL in a reverse cholesterol transport pathway is to transport and deliver an excess of cholesterol, which is left over after having been used by peripheral cells, to a liver tissue. The cholesterol delivered to the liver tissue may be uptaken into the inside of hepatocytes through a cholesterol recognizing receptor, scavenger receptor(B-I), and undergo a degradation metabolism. rHDLs were synthesized using the apoA-I mutants of the present invention at a molar ratio of phospholipid:cholesterol:apoA-I being 95:5:1 according to the same method as described in Example 13 except that NBD-cholesterol having a fluorescence was added at a molar ratio of 100:1 as compared with free cholesterol. Therefore, it was possible to compare the efficiencies of delivering cholesterol into the cell interior by tracking the fluorescence of cholesterol in rHDLs. Hepatic cell line, HepG2 cells were treated with the same amount of rHDL and incubated at 37° C. for 18-24 hrs. The cells were washed three times with PBS, and the amount of cholesterol uptaken into the cell interior was measured with a confocal fluorescence scanning microscope.

As shown in FIG. 17, V156K-rHDL showed the highest delivering activity of cholesterol to hepatocytes, and A158E-rHDL also showed higher delivering activity than the WT-rHDL. Further, V156K showed higher delivering activity than apoA-I Milano. The upper photograph of FIG. 17 is to take a photograph with a fluorescent filter(Ex=488 nm, Em=540 nm) to detect NBD-chloesterol, and the lower photograph is to take a photograph with an optical DIC to observe the cell's shape. FIG. 17 showed that despite the same number of cells and shape thereof, the levels of delivering cholesterol into the cell interior were different depending on the kinds of rHDLs.

In order to confirm the above results, the whole fluorescence at a bottom of the plate to which the cells adhered was removed by washing the plate with PBS, and only the amount of fluorescence uptaken into the cells was measured with an optical microplate reader(Victor2 optical microplate reader, Perkin Elmer, Ex=460 nm, Em=534 nm). As a result, as illustrated in FIG. 18, V156K-rHDL showed the highest activity for delivering cholesterol between the reaction time ranging from 3 to 18 hrs, e.g., 4-fold or more higher than the WT-rHDL, and A158E-rHDL showed 2-fold higher delivering activity than the WT-rHDL. These results coincided well with those observed with a fluorescence scanning microscope. R173C-apoA-I(apoA-I Milano) showed higher inflow of cholesterol into the cell interior from the beginning to 6 hrs after the cultivation than the WT-rHDL and A158E-rHDL, but the inflow of cholesterol became decreased from 12 hrs after the cultivation and, finally, it showed lower delivering activity than A158E-rHDL upto 18 hrs. Accordingly, V156K-propao A-I-rHDL and A158E-proapoA-I-rHDL of the present invention showed superior cholesterol delivering activity to the previously reported R173C-apoA-I.

In order to confirm these results, rHDLs(1 mg/mL of apoA-I) containing radioactive isotope-labeled cholesterol, [$^{14}$C]-cholesterol, were synthesized for each mutants according to the same method as described in Example 13, and HepG2 cells(1 mL of medium, 6-well plate) were treated with the synthesized rHDLs, respectively. The cell samples were taken from the culture solution at regular intervals from immediately to 18 hrs after the treatment and were centrifuged to separate cell pellets and discard the culture medium. The cells thus recovered were subjected to alkali degradation to disrupt their membrane, and stirred to expose all cytoplasm, and, then, subjected to scintillation counting to measure their radioactivities. When treated with the same concentration of rHDL, the amount of cholesterol delivered into the cells by each proapoA-I mutant was compared with that by the WT proapoA-I by using the measured radioactivities.

As shown in FIGS. 16 and 17, V156K- and A158E-rHDLs showed 30% or higher efficiencies for delivering cholesterol than the WT-rHDL during the treatment for 18 hrs. This result coincided with that of FIG. 18, which demonstrates that the efficiencies of V156K- and A158E-rHDLs for delivering blood cholesterol into hepatocytes through scavenger receptor B-I are superior to those of the WT proapoA-I and R173C-apoA-I(apoA-I Milano).

Further, the sixth helix domain(143-164 amino acid) which plays an important role in major functions of apoA-I such as hinge domain movement, LCAT activation and maintenance of rHDL's particle structure was analyzed with Protean 5.0.7 softwear(DNASTAR, USA) to estimate the role of proapoA-I mutants of the present invention within the domain. As illustrated in FIG. 19, when look down the sixth helix domain of apoA-I from the top of a helical axis, it was represented as a typically amphiphatic helix in which the distribution of non polar amino acids(hydrophobic amino acids) is symmetrical to that of polar amino acids (hydrophilic amino acids). Hydrophobic amino acids, Val156 and Ala158 located at a symmetric point of the hydrophobic residue region and the hydrophilic residue region as underlined were replaced by (+) charged amino acid and (−) charged amino acid, respectively, to examine the change when disturbed the arrangement of amphiphatic helix. If these two amino acids were replaced by other amino acids having a strong electric charge like the above, it has been expected that amphiphillicity of V156K or A158E may be destroyed, and electrostatic repulsion between Arg149 and Lys156 of V156K and between Glu147 and Glu158 of A158E may occur a structural change of the domain.

As a result, proapoA-I-V156K and proapoA-I-A158E showed superior pharmacological effects to the WT proapoA-I due to the difference in their structures, e.g., higher LDL-antioxidant activity(Example 8), enlarged rHDL size(Example 12), lost of LCAT activation efficiency (Example 14), and improved cholesterol delivering activity (into hepatocytes, Example 15).

EXAMPLE 16

Parenteral Administration Test for Acute Toxicity Using Rat

Acute toxicity was examined using 6-week-old specific pathogen free(SPF) SD type rats. Each of proapoA-I mutants were suspended in 0.5% methylcellulose solution, and each resulting suspension was orally administered to two rats per experimental group at a dose of 1 g/kg/mL. After the administration, rats were observed in terms of clinic symptom and change in weights of rats, and brought to blood test and autopsy so as to investigate the abnormalities of abdominal and thoracic organs. As a result, all tested animals were survived, and there was no striking clinic symptom, change in weights or other toxic effect. All the examined compounds did not elicit any toxic effect when administered to rats within the range of 500 mg/kg, thus proved to be safe compounds for parenteral administration.

PREPARATION EXAMPLE 1

Preparation of an Injection injection(based on 2 mL):

| | |
|---|---|
| proapoA-I mutant | 100 mg |
| sodium chloride | 18 mg |
| benzyl alcohol | 45 mg |
| distilled water for injection | 2 mL |

Each of proapoA-I mutants of the present invention was dissolved in a solvent as described above, and the resulting solution was subjected to filtration using a membrane filter until it becomes transparent. After the filtration, the filtrate was filled into an ampoule and completely sterilized by a high pressure steam sterilizer.

What is claimed is:

1. An isolated polypeptide consisting SEQ ID NO:21.
2. An isolated polypeptide comprising of SEQ ID NO:21.
3. A pharmaceutical composition comprising the polypeptide of claim 1 or 2 for treatment of hyperlipidemia.
4. A pharmaceutical composition comprising the polypeptide of claim 1 or 2 for treatment of atherosclerosis.
5. A method of treating hyperlipidemia comprising administering the pharmaceutical composition of claim 3.
6. A method of treating atherosclerosis comprising administering the pharmaceutical composition of claim 4.

* * * * *

UNITED STATES PATENT AND TRADEMARK OFFICE
CERTIFICATE OF CORRECTION

PATENT NO. : 7,273,849 B2
APPLICATION NO. : 11/116319
DATED : September 25, 2007
INVENTOR(S) : Kyung-Hyun Cho It is certified that error appears in the above-identified patent and that said Letters Patent is hereby corrected as shown below:

Title page, item (54), line 1 of title,
"PROAPOLIPOPROTEINA-I MUTANT AND" should read
--PROAPOLIPOPROTEIN A-I MUTANT AND--.

Claim 1, col. 37, line 24,
"An isolated polypeptide consisting SEQ ID NO:21." should read
--An isolated polypeptide consisting of SEQ ID NO:21.--

Claim 2, col. 37, line 25,
"An isolated polypeptide comprising of SEQ ID NO:21." should read
--An isolated polypeptide comprising SEQ ID NO:21.--.

Signed and Sealed this

Twenty-ninth Day of July, 2008

JON W. DUDAS
*Director of the United States Patent and Trademark Office*

UNITED STATES PATENT AND TRADEMARK OFFICE
CERTIFICATE OF CORRECTION

PATENT NO.        : 7,273,849 B2
APPLICATION NO.   : 11/116319
DATED             : September 25, 2007
INVENTOR(S)       : Kyung-Hyun Cho It is certified that error appears in the above-identified patent and that said Letters Patent is hereby corrected as shown below:

Title page, item (54), line 1 of title, and Column 1, line 1,
"PROAPOLIPOPROTEINA-I MUTANT AND" should read
--PROAPOLIPOPROTEIN A-I MUTANT AND--.

Claim 1, col. 37, line 24,
"An isolated polypeptide consisting SEQ ID NO:21." should read
--An isolated polypeptide consisting of SEQ ID NO:21.--

Claim 2, col. 37, line 25,
"An isolated polypeptide comprising of SEQ ID NO:21." should read
--An isolated polypeptide comprising SEQ ID NO:21.--.

This certificate supersedes the Certificate of Correction issued July 29, 2008.

Signed and Sealed this

Twenty-sixth Day of August, 2008

JON W. DUDAS
*Director of the United States Patent and Trademark Office*

SEQUENCE LISTING

```
<160> NUMBER OF SEQ ID NOS: 23

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
 1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
        50                  55                  60

Gly Pro Val Thr Gln Glu Phe Trp Asp Asn Leu Glu Lys Glu Thr Glu
    65                  70                  75                  80
```

-continued

```
Gly Leu Arg Gln Glu Met Ser Lys Asp Leu Glu Val Lys Ala Lys
             85                  90                  95

Val Gln Pro Tyr Leu Asp Asp Phe Gln Lys Lys Trp Gln Glu Met
        100                 105                 110

Glu Leu Tyr Arg Gln Lys Val Glu Pro Leu Arg Ala Glu Leu Gln Glu
    115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 301
<212> TYPE: PRT
<213> ORGANISM: Homo sapiens

<400> SEQUENCE: 2

Met His His His His His Ser Ser Gly Leu Val Pro Arg Gly Ser
  1               5                  10                  15

Gly Met Lys Glu Thr Ala Ala Ala Lys Phe Glu Arg Gln His Met Asp
             20                  25                  30

Ser Pro Asp Leu Gly Thr Asp Asp Asp Lys Ala Met Ala His Phe
         35                  40                  45

Trp Gln Gln Ala Pro Arg Pro Pro Thr Pro Asp Glu Pro Gln Ser
     50                  55                  60

Pro Trp Asp Arg Val Lys Asp Leu Ala Thr Val Tyr Val Asp Val Leu
 65                  70                  75                  80

Lys Asp Ser Gly Arg Asp Tyr Val Ser Gln Phe Glu Gly Ser Ala Leu
                 85                  90                  95

Gly Lys Gln Leu Asn Leu Lys Leu Leu Asp Asn Trp Asp Ser Val Thr
            100                 105                 110

Ser Thr Phe Ser Lys Leu Arg Glu Gln Leu Gly Pro Val Thr Gln Glu
        115                 120                 125

Phe Trp Asp Asn Leu Glu Lys Glu Thr Glu Gly Leu Arg Gln Glu Met
    130                 135                 140

Ser Lys Asp Leu Glu Glu Val Lys Ala Lys Val Gln Pro Tyr Leu Asp
145                 150                 155                 160

Asp Phe Gln Lys Lys Trp Gln Glu Met Glu Leu Tyr Arg Gln Lys
                165                 170                 175

Val Glu Pro Leu Arg Ala Glu Leu Gln Glu Gly Ala Arg Gln Lys Leu
            180                 185                 190

His Glu Leu Gln Glu Lys Leu Ser Pro Leu Gly Glu Glu Met Arg Asp
        195                 200                 205
```

```
Arg Ala Arg Ala His Val Asp Ala Leu Arg Thr His Leu Ala Pro Tyr
    210                 215                 220

Ser Asp Glu Leu Arg Gln Arg Leu Ala Ala Arg Leu Glu Ala Leu Lys
225                 230                 235                 240

Glu Asn Gly Gly Ala Arg Leu Ala Glu Tyr His Ala Lys Ala Thr Glu
                245                 250                 255

His Leu Ser Thr Leu Ser Glu Lys Ala Lys Pro Ala Leu Glu Asp Leu
                260                 265                 270

Arg Gln Gly Leu Leu Pro Val Leu Glu Ser Phe Lys Val Ser Phe Leu
                275                 280                 285

Ser Ala Leu Glu Glu Tyr Thr Lys Lys Leu Asn Thr Gln
290                 295                 300

<210> SEQ ID NO 3
<211> LENGTH: 795
<212> TYPE: DNA
<213> ORGANISM: Homo sapiens

<400> SEQUENCE: 3
cgacgacgac gacaaggcca tggcccattt ctggcagcaa gctccacgtc caccgacacc      60
cgatgaaccc ccccagagcc cctgggatcg agtgaaggac ctggccactg tgtacgtgga    120
tgtgctcaaa gacagcggca gagactatgt gtcccagttt gaaggctccg ccttgggaaa    180
acagctaaac ctaaaacttc tagacaactg ggacagcgtg acctccacct tcagcaagct    240
gcgcgaacag ctcggccctg tgacccagga attctgggat aacctggaaa aggagacaga    300
gggcctgagg caggagatga gcaaggatct ggaggaggtg aaggccaagg tgcagcccta    360
cctggacgac ttccagaaga gtggcagga ggagatggag ctctaccgcc agaaggtgga    420
gccgctgcgc gcagagctgc aggagggcgc gcgccagaag ctgcacgagc tgcaagagaa    480
gctgagccca ctgggcgagg agatgcgcga ccgcgcgcgc gcccatgtgg acgcgctccg    540
gacgcatctg gccccctaca gcgacgagct gcgccagcgc ttggccgcgc gccttgaggc    600
tctcaaggag aacggcggcg ccaggctagc cgagtaccac gccaaggcca ccgagcatct    660
gagcacgctc agcgagaagg ccaagcccgc gctcgaggac ctccgccaag gcctgctgcc    720
cgtgctggag agcttcaagg tcagcttcct gagcgctctc gaggagtaca ctaagaagct    780
caacacccag taata                                                    795

<210> SEQ ID NO 4
<211> LENGTH: 36
<212> TYPE: DNA
<213> ORGANISM: Artificial Sequence
<220> FEATURE:
<223> OTHER INFORMATION: sense primer of proapoA-I-A154E

<400> SEQUENCE: 4
atgcgcgacc gcgcgcgcga acatgtggac gcgctc                              36

<210> SEQ ID NO 5
<211> LENGTH: 36
<212> TYPE: DNA
<213> ORGANISM: Artificial Sequence
<220> FEATURE:
<223> OTHER INFORMATION: antisense primer of proapoA-I-A154E

<400> SEQUENCE: 5
gagcgcgtcc acatgttcgc gcgcgcggtc gcgcat                              36
```

```
<210> SEQ ID NO 6
<211> LENGTH: 36
<212> TYPE: DNA
<213> ORGANISM: Artificial Sequence
<220> FEATURE:
<223> OTHER INFORMATION: sense primer of proapoA-I-H155E

<400> SEQUENCE: 6
cgcgatcgcg cgcgagcgga agtcgacgcc ctccgg                              36

<210> SEQ ID NO 7
<211> LENGTH: 36
<212> TYPE: DNA
<213> ORGANISM: Artificial Sequence
<220> FEATURE:
<223> OTHER INFORMATION: antisense primer of proapoA-I-H155E

<400> SEQUENCE: 7
ccggagggcg tcgacttccg ctcgcgcgcg atcgcg                              36

<210> SEQ ID NO 8
<211> LENGTH: 36
<212> TYPE: DNA
<213> ORGANISM: Artificial Sequence
<220> FEATURE:
<223> OTHER INFORMATION: sense primer of proapoA-I-V156K

<400> SEQUENCE: 8
gaccgcgccc gggcccataa ggacgcgctc cggacg                              36

<210> SEQ ID NO 9
<211> LENGTH: 36
<212> TYPE: DNA
<213> ORGANISM: Artificial Sequence
<220> FEATURE:
<223> OTHER INFORMATION: antisense primer of proapoA-I-V156K

<400> SEQUENCE: 9
cgtccggagc gcgtccttat gggcccgggc gcggtc                              36

<210> SEQ ID NO 10
<211> LENGTH: 36
<212> TYPE: DNA
<213> ORGANISM: Artificial Sequence
<220> FEATURE:
<223> OTHER INFORMATION: sense primer of proapoA-I-D157K

<400> SEQUENCE: 10
cgcgcgcgcg cacacgtgaa ggcgctccgg acgcat                              36

<210> SEQ ID NO 11
<211> LENGTH: 36
<212> TYPE: DNA
<213> ORGANISM: Artificial Sequence
<220> FEATURE:
<223> OTHER INFORMATION: antisense primer of proapoA-I-D157K

<400> SEQUENCE: 11
atgcgtccgg agcgccttca cgtgtgcgcg cgcgcg                              36

<210> SEQ ID NO 12
<211> LENGTH: 36
<212> TYPE: DNA
<213> ORGANISM: Artificial Sequence
<220> FEATURE:
<223> OTHER INFORMATION: sense primer of proapoA-I-A158E
```

```
<400> SEQUENCE: 12
gcgcgcgcac acgtggacga actccggacg cacctg                            36

<210> SEQ ID NO 13
<211> LENGTH: 36
<212> TYPE: DNA
<213> ORGANISM: Artificial Sequence
<220> FEATURE:
<223> OTHER INFORMATION: antisense primer of proapoA-I-A158E

<400> SEQUENCE: 13
caggtgcgtc cggagttcgt ccacgtgtgc gcgcgc                            36

<210> SEQ ID NO 14
<211> LENGTH: 774
<212> TYPE: DNA
<213> ORGANISM: Artificial Sequence
<220> FEATURE:
<223> OTHER INFORMATION: proapoA-I-A154E

<400> SEQUENCE: 14
gccatggccc atttctggca gcaagctcca cgtccaccga cacccgatga accccccag    60 agcccctggg atcgagtgaa ggacctggcc actgtgtacg tggatgtgct caaagacagc   120
ggcagagact atgtgtccca gtttgaaggc tccgccttgg aaaacagct aaacctaaaa   180 cttctagaca actgggacag cgtgacctcc accttcagca agctgcgcga acagctcggc   240
cctgtgaccc aggaattctg gataaacctg gaaaaggaga cagagggcct gaggcaggag   300
atgagcaagg atctggagga ggtgaaggcc aaggtgcagc cctacctgga cgacttccag   360
aagaagtggc aggaggagat ggagctctac cgccagaagg tggagccgct gcgcgcagag   420
ctgcaggagg gcgcgcgcca gaagctgcac gagctgcaag agaagctgag cccactgggc   480
gaggagatgc gcgaccgcgc gcgcgaacat gtggacgcgc tccggacgca tctggccccc   540
tacagcgacg agctgcgcca gcgcttggcc gcgcgccttg aggctctcaa ggagaacggc   600
ggcgccaggc tagccgagta ccacgccaag gccaccgagc atctgagcac gctcagcgag   660
aaggccaagc ccgcgctcga ggacctccgc caaggcctgc tgcccgtgct ggagagcttc   720
aaggtcagct tcctgagcgc tctcgaggag tacactaaga agctcaacac ccag         774

<210> SEQ ID NO 15
<211> LENGTH: 774
<212> TYPE: DNA
<213> ORGANISM: Artificial Sequence
<220> FEATURE:
<223> OTHER INFORMATION: proapoA-I-H155E

<400> SEQUENCE: 15
gccatggccc atttctggca gcaagctcca cgtccaccga cacccgatga accccccag    60 agcccctggg atcgagtgaa ggacctggcc actgtgtacg tggatgtgct caaagacagc   120
ggcagagact atgtgtccca gtttgaaggc tccgccttgg aaaacagct aaacctaaaa   180 cttctagaca actgggacag cgtgacctcc accttcagca agctgcgcga acagctcggc   240
cctgtgaccc aggaattctg gataaacctg gaaaaggaga cagagggcct gaggcaggag   300
atgagcaagg atctggagga ggtgaaggcc aaggtgcagc cctacctgga cgacttccag   360
aagaagtggc aggaggagat ggagctctac cgccagaagg tggagccgct gcgcgcagag   420
ctgcaggagg gcgcgcgcca gaagctgcac gagctgcaag agaagctgag cccactgggc   480
gaggagatgc gcgatcgcgc gcgagcggaa gtcgacgccc tccggacgca tctggccccc   540
```

```
tacagcgacg agctgcgcca gcgcttggcc gcgcgccttg aggctctcaa ggagaacggc    600
ggcgccaggc tagccgagta ccacgccaag gccaccgagc atctgagcac gctcagcgag    660
aaggccaagc ccgcgctcga ggacctccgc caaggcctgc tgcccgtgct ggagagcttc    720
aaggtcagct tcctgagcgc tctcgaggag tacactaaga agctcaacac ccag          774

<210> SEQ ID NO 16
<211> LENGTH: 774
<212> TYPE: DNA
<213> ORGANISM: Artificial Sequence
<220> FEATURE:
<223> OTHER INFORMATION: proapoA-I-V156K

<400> SEQUENCE: 16
gccatggccc atttctggca gcaagctcca cgtccaccga cacccgatga acccccccag    60
agcccctggg atcgagtgaa ggacctggcc actgtgtacg tggatgtgct caaagacagc    120
ggcagagact atgtgtccca gtttgaaggc tccgccttgg aaaacagct aaacctaaaa     180 cttctagaca actgggacag cgtgacctcc accttcagca agctgcgcga acagctcggc    240
cctgtgaccc aggaattctg ggataaacctg aaaaggaga cagagggcct gaggcaggag    300
atgagcaagg atctggagga ggtgaaggcc aaggtgcagc cctacctgga cgacttccag    360
aagaagtggc aggaggagat ggagctctac cgccagaagg tggagccgct gcgcgcagag    420
ctgcaggagg gcgcgcgcca gaagctgcac gagctgcaag agaagctgag cccactgggc    480
gaggagatgc gcgaccgcgc ccgggcccat aaggacgcgc tccggacgca tctggccccc    540
tacagcgacg agctgcgcca gcgcttggcc gcgcgccttg aggctctcaa ggagaacggc    600
ggcgccaggc tagccgagta ccacgccaag gccaccgagc atctgagcac gctcagcgag    660
aaggccaagc ccgcgctcga ggacctccgc caaggcctgc tgcccgtgct ggagagcttc    720
aaggtcagct tcctgagcgc tctcgaggag tacactaaga agctcaacac ccag          774

<210> SEQ ID NO 17
<211> LENGTH: 774
<212> TYPE: DNA
<213> ORGANISM: Artificial Sequence
<220> FEATURE:
<223> OTHER INFORMATION: proapoA-I-D157K

<400> SEQUENCE: 17
gccatggccc atttctggca gcaagctcca cgtccaccga cacccgatga acccccccag    60
agcccctggg atcgagtgaa ggacctggcc actgtgtacg tggatgtgct caaagacagc    120
ggcagagact atgtgtccca gtttgaaggc tccgccttgg aaaacagct aaacctaaaa     180 cttctagaca actgggacag cgtgacctcc accttcagca agctgcgcga acagctcggc    240
cctgtgaccc aggaattctg ggataaacctg aaaaggaga cagagggcct gaggcaggag    300
atgagcaagg atctggagga ggtgaaggcc aaggtgcagc cctacctgga cgacttccag    360
aagaagtggc aggaggagat ggagctctac cgccagaagg tggagccgct gcgcgcagag    420
ctgcaggagg gcgcgcgcca gaagctgcac gagctgcaag agaagctgag cccactgggc    480
gaggagatgc gcgaccgcgc gcgcgcacac gtgaaggcgc tccggacgca tctggccccc    540
tacagcgacg agctgcgcca gcgcttggcc gcgcgccttg aggctctcaa ggagaacggc    600
ggcgccaggc tagccgagta ccacgccaag gccaccgagc atctgagcac gctcagcgag    660
aaggccaagc ccgcgctcga ggacctccgc caaggcctgc tgcccgtgct ggagagcttc    720
```

```
aaggtcagct tcctgagcgc tctcgaggag tacactaaga agctcaacac ccag        774
```

<210> SEQ ID NO 18
<211> LENGTH: 774
<212> TYPE: DNA
<213> ORGANISM: Artificial Sequence
<220> FEATURE:
<223> OTHER INFORMATION: proapoA-I-A158E

<400> SEQUENCE: 18

```
gccatggccc atttctggca gcaagctcca cgtccaccga cacccgatga acccccccag   60
agccctgggg atcgagtgaa ggacctggcc actgtgtacg tggatgtgct caaagacagc  120
ggcagagact atgtgtccca gtttgaaggc tccgccttgg gaaaacagct aaacctaaaa  180
cttctagaca actgggacag cgtgacctcc accttcagca agctgcgcga acagctcggc  240
cctgtgaccc aggaattctg ggataacctg gaaaaggaga cagagggcct gaggcaggag  300
atgagcaagg atctggagga ggtgaaggcc aaggtgcagc cctacctgga cgacttccag  360
aagaagtggc aggaggagat ggagctctac cgccagaagg tggagccgct gcgcgcagag  420
ctgcaggagg gcgcgcgcca gaagctgcac gagctgcaag agaagctgag cccactgggc  480
gaggagatgc gcgaccgcgc gcgcgcacac gtggacgaac tccggacgca cctggccccc  540
tacagcgacg agctgcgcca gcgcttggcc gcgcgccttg aggctctcaa ggagaacggc  600
ggcgccaggc tagccgagta ccacgccaag gccaccgagc atctgagcac gctcagcgag  660
aaggccaagc ccgcgctcga ggacctccgc caaggcctgc tgcccgtgct ggagagcttc  720
aaggtcagct tcctgagcgc tctcgaggag tacactaaga agctcaacac ccag        774
```

<210> SEQ ID NO 19
<211> LENGTH: 258
<212> TYPE: PRT
<213> ORGANISM: Artificial Sequence
<220> FEATURE:
<223> OTHER INFORMATION: proapoA-I-A154E

<400> SEQUENCE: 19

```
Ala Met Ala His Phe Trp Gln Gln Ala Pro Arg Pro Pro Thr Pro Asp
  1               5                  10                  15

Glu Pro Pro Gln Ser Pro Trp Asp Arg Val Lys Asp Leu Ala Thr Val
             20                  25                  30

Tyr Val Asp Val Leu Lys Asp Ser Gly Arg Asp Tyr Val Ser Gln Phe
         35                  40                  45

Glu Gly Ser Ala Leu Gly Lys Gln Leu Asn Leu Lys Leu Leu Asp Asn
     50                  55                  60

Trp Asp Ser Val Thr Ser Thr Phe Ser Lys Leu Arg Glu Gln Leu Gly
 65                  70                  75                  80

Pro Val Thr Gln Glu Phe Trp Asp Asn Leu Glu Lys Glu Thr Glu Gly
                 85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
        115                 120                 125

Leu Tyr Arg Gln Lys Val Glu Pro Leu Arg Ala Glu Leu Gln Glu Gly
    130                 135                 140

Ala Arg Gln Lys Leu His Glu Leu Gln Glu Lys Leu Ser Pro Leu Gly
145                 150                 155                 160

Glu Glu Met Arg Asp Arg Ala Arg Glu His Val Asp Ala Leu Arg Thr
```

```
                165                 170                 175
His Leu Ala Pro Tyr Ser Asp Glu Leu Arg Gln Arg Leu Ala Ala Arg
            180                 185                 190

Leu Glu Ala Leu Lys Glu Asn Gly Gly Ala Arg Leu Ala Glu Tyr His
            195                 200                 205

Ala Lys Ala Thr Glu His Leu Ser Thr Leu Ser Glu Lys Ala Lys Pro
            210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
            245                 250                 255

Thr Gln

<210> SEQ ID NO 20
<211> LENGTH: 258
<212> TYPE: PRT
<213> ORGANISM: Artificial Sequence
<220> FEATURE:
<223> OTHER INFORMATION: proapoA-I-H155E

<400> SEQUENCE: 20

Ala Met Ala His Phe Trp Gln Gln Ala Pro Arg Pro Thr Pro Asp
1               5                   10                  15

Glu Pro Pro Gln Ser Pro Trp Asp Arg Val Lys Asp Leu Ala Thr Val
            20                  25                  30

Tyr Val Asp Val Leu Lys Asp Ser Gly Arg Asp Tyr Val Ser Gln Phe
            35                  40                  45

Glu Gly Ser Ala Leu Gly Lys Gln Leu Asn Leu Lys Leu Leu Asp Asn
        50                  55                  60

Trp Asp Ser Val Thr Ser Thr Phe Ser Lys Leu Arg Glu Gln Leu Gly
65                  70                  75                  80

Pro Val Thr Gln Glu Phe Trp Asp Asn Leu Glu Lys Glu Thr Glu Gly
                85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
            115                 120                 125

Leu Tyr Arg Gln Lys Val Glu Pro Leu Arg Ala Glu Leu Gln Glu Gly
            130                 135                 140

Ala Arg Gln Lys Leu His Glu Leu Gln Glu Lys Leu Ser Pro Leu Gly
145                 150                 155                 160

Glu Glu Met Arg Asp Arg Ala Arg Ala Glu Val Asp Ala Leu Arg Thr
            165                 170                 175

His Leu Ala Pro Tyr Ser Asp Glu Leu Arg Gln Arg Leu Ala Ala Arg
            180                 185                 190

Leu Glu Ala Leu Lys Glu Asn Gly Gly Ala Arg Leu Ala Glu Tyr His
            195                 200                 205

Ala Lys Ala Thr Glu His Leu Ser Thr Leu Ser Glu Lys Ala Lys Pro
            210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
            245                 250                 255

Thr Gln
```

<210> SEQ ID NO 21
<211> LENGTH: 258
<212> TYPE: PRT
<213> ORGANISM: Artificial Sequence
<220> FEATURE:
<223> OTHER INFORMATION: proapoA-I-V156K

<400> SEQUENCE: 21

```
Ala Met Ala His Phe Trp Gln Gln Ala Pro Arg Pro Thr Pro Asp
 1               5                  10                  15

Glu Pro Pro Gln Ser Pro Trp Asp Arg Val Lys Asp Leu Ala Thr Val
                20                  25                  30

Tyr Val Asp Val Leu Lys Asp Ser Gly Arg Asp Tyr Val Ser Gln Phe
            35                  40                  45

Glu Gly Ser Ala Leu Gly Lys Gln Leu Asn Leu Lys Leu Leu Asp Asn
50                  55                  60

Trp Asp Ser Val Thr Ser Thr Phe Ser Lys Leu Arg Glu Gln Leu Gly
65                  70                  75                  80

Pro Val Thr Gln Glu Phe Trp Asp Asn Leu Glu Lys Glu Thr Glu Gly
                85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
        115                 120                 125

Leu Tyr Arg Gln Lys Val Glu Pro Leu Arg Ala Glu Leu Gln Glu Gly
130                 135                 140

Ala Arg Gln Lys Leu His Glu Leu Gln Glu Lys Leu Ser Pro Leu Gly
145                 150                 155                 160

Glu Glu Met Arg Asp Arg Ala Arg Ala His Lys Asp Ala Leu Arg Thr
                165                 170                 175

His Leu Ala Pro Tyr Ser Asp Glu Leu Arg Gln Arg Leu Ala Ala Arg
            180                 185                 190

Leu Glu Ala Leu Lys Glu Asn Gly Gly Ala Arg Leu Ala Glu Tyr His
        195                 200                 205

Ala Lys Ala Thr Glu His Leu Ser Thr Leu Ser Glu Lys Ala Lys Pro
210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
                245                 250                 255

Thr Gln
```

<210> SEQ ID NO 22
<211> LENGTH: 258
<212> TYPE: PRT
<213> ORGANISM: Artificial Sequence
<220> FEATURE:
<223> OTHER INFORMATION: proapoA-I-D157K

<400> SEQUENCE: 22

```
Ala Met Ala His Phe Trp Gln Gln Ala Pro Arg Pro Thr Pro Asp
 1               5                  10                  15

Glu Pro Pro Gln Ser Pro Trp Asp Arg Val Lys Asp Leu Ala Thr Val
                20                  25                  30

Tyr Val Asp Val Leu Lys Asp Ser Gly Arg Asp Tyr Val Ser Gln Phe
            35                  40                  45
```

-continued

```
Glu Gly Ser Ala Leu Gly Lys Gln Leu Asn Leu Lys Leu Leu Asp Asn
 50                  55                  60

Trp Asp Ser Val Thr Ser Thr Phe Ser Lys Leu Arg Glu Gln Leu Gly
 65                  70                  75                  80

Pro Val Thr Gln Glu Phe Trp Asp Asn Leu Glu Lys Glu Thr Glu Gly
                 85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
        115                 120                 125

Leu Tyr Arg Gln Lys Val Glu Pro Leu Arg Ala Glu Leu Gln Glu Gly
130                 135                 140

Ala Arg Gln Lys Leu His Glu Leu Gln Glu Lys Leu Ser Pro Leu Gly
145                 150                 155                 160

Glu Glu Met Arg Asp Arg Ala Arg Ala His Val Lys Ala Leu Arg Thr
                165                 170                 175

His Leu Ala Pro Tyr Ser Asp Glu Leu Arg Gln Arg Leu Ala Ala Arg
            180                 185                 190

Leu Glu Ala Leu Lys Glu Asn Gly Gly Ala Arg Leu Ala Glu Tyr His
        195                 200                 205

Ala Lys Ala Thr Glu His Leu Ser Thr Leu Ser Glu Lys Ala Lys Pro
210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
                245                 250                 255

Thr Gln
```

<210> SEQ ID NO 23
<211> LENGTH: 258
<212> TYPE: PRT
<213> ORGANISM: Artificial Sequence
<220> FEATURE:
<223> OTHER INFORMATION: proapoA-I-A158E

<400> SEQUENCE: 23

```
Ala Met Ala His Phe Trp Gln Gln Ala Pro Arg Pro Thr Pro Asp
 1               5                  10                  15

Glu Pro Pro Gln Ser Pro Trp Asp Arg Val Lys Asp Leu Ala Thr Val
                 20                  25                  30

Tyr Val Asp Val Leu Lys Asp Ser Gly Arg Asp Tyr Val Ser Gln Phe
            35                  40                  45

Glu Gly Ser Ala Leu Gly Lys Gln Leu Asn Leu Lys Leu Leu Asp Asn
        50                  55                  60

Trp Asp Ser Val Thr Ser Thr Phe Ser Lys Leu Arg Glu Gln Leu Gly
 65                  70                  75                  80

Pro Val Thr Gln Glu Phe Trp Asp Asn Leu Glu Lys Glu Thr Glu Gly
                 85                  90                  95

Leu Arg Gln Glu Met Ser Lys Asp Leu Glu Glu Val Lys Ala Lys Val
            100                 105                 110

Gln Pro Tyr Leu Asp Asp Phe Gln Lys Lys Trp Gln Glu Glu Met Glu
        115                 120                 125

Leu Tyr Arg Gln Lys Val Glu Pro Leu Arg Ala Glu Leu Gln Glu Gly
130                 135                 140

Ala Arg Gln Lys Leu His Glu Leu Gln Glu Lys Leu Ser Pro Leu Gly
```

-continued

```
            145                 150                 155                 160
Glu Glu Met Arg Asp Arg Ala Arg Ala His Val Asp Glu Leu Arg Thr
                165                 170                 175

His Leu Ala Pro Tyr Ser Asp Glu Leu Arg Gln Arg Leu Ala Ala Arg
                180                 185                 190

Leu Glu Ala Leu Lys Glu Asn Gly Gly Ala Arg Leu Ala Glu Tyr His
            195                 200                 205

Ala Lys Ala Thr Glu His Leu Ser Thr Leu Ser Glu Lys Ala Lys Pro
        210                 215                 220

Ala Leu Glu Asp Leu Arg Gln Gly Leu Leu Pro Val Leu Glu Ser Phe
225                 230                 235                 240

Lys Val Ser Phe Leu Ser Ala Leu Glu Glu Tyr Thr Lys Lys Leu Asn
                245                 250                 255

Thr Gln
```